United States Patent
Gernez et al.

(10) Patent No.: US 9,891,213 B2
(45) Date of Patent: *Feb. 13, 2018

(54) GRANULOCYTE-BASED METHODS FOR DETECTING AND MONITORING IMMUNE SYSTEM DISORDERS

(75) Inventors: Yael Gernez, San Francisco, CA (US); Leonore A. Herzenberg, Stanford, CA (US); Kari Nadeau, Stanford, CA (US); Rabindra Tirouvanziam, Decatur, GA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 529 days.

This patent is subject to a terminal disclaimer.

(21) Appl. No.: 12/686,121

(22) Filed: Jan. 12, 2010

(65) Prior Publication Data

US 2010/0209950 A1 Aug. 19, 2010

Related U.S. Application Data

(60) Provisional application No. 61/144,152, filed on Jan. 12, 2009.

(51) Int. Cl.
*G01N 33/50* (2006.01)

(52) U.S. Cl.
CPC ..... *G01N 33/5094* (2013.01); *G01N 2800/24* (2013.01)

(58) Field of Classification Search
None
See application file for complete search history.

(56) References Cited

PUBLICATIONS

Ebo et al., "Flow Cytometric Analysis of In Vitro Activated Basophils, Specific IgE and Skin Tests in the Diagnosis of Pollen-Associated Food Allergy,"(Cytometry Part B (Clinical Cytometry), vol. 64B, pp. 28-33; 2005).*
Perez et al., "Phospho-proteomic immune analysis by flow cytometry: from mechanism to translational medicine at the single-cell level," (Immunological Reviews, vol. 210, pp. 208-228; 2006).*
Mecknache et al., Journal of Immunology, vol. 182, pp. 2542-2550; 2009.*
Dijkstra et al., Nature Medicine, vol. 18, No. 4, pp. 488-489, 2012.*
Eades-Perner et al., Blood, vol. 91, No. 2, pp. 663-672; 1998.*
Roskoski, R., Biochemical and Biophysical Research Communications, vol. 331, pp. 1-14; 2005.*
MacDonald et al., Molecular Immunology, vol. 38, pp. 1323-1327; 2001.*
Gibbs et al., Journal of Allergy and Clinical Immunology, vol. 118, No. 5, pp. 1060-1067; Sep. 12, 2006.*
Perez et al., Immunological Reviews, vol. 210, pp. 208-228; 2006 (of record).*
Mecknache et al., Journal of Immunology, vol. 182, pp. 2542-2550; 2009 (of record).*
Dijkstra et al., Nature Medicine, vol. 18, No. 4, pp. 488-489, 2012 (of record).*
Eades-Perner et al., Blood, vol. 91, No. 2, pp. 663-672; 1998 (of record).*
Roskoski, R., Biochemical and Biophysical Research Communications, vol. 331, pp. 1-14; 2005 (of record).*
MacDonald et al., Molecular Immunology, vol. 38, pp. 1323-1327; 2001 (of record).*
Gibbs et al., Journal of Allergy and Clinical Immunology, vol. 118, No. 5, pp. 1060-1067; Sep. 12, 2006 (of record).*
Ortolani et al., Allergy, vol. 53, Suppl. 46, pp. 58-61; 1998.*
Aerts et al., Cytometry Part B (Clinical Cytometry), vol. 76B, pp. 8-17; published online Aug. 25, 2008 (of record).*
Ebo et al., Clinical and Experimental Allergy, vol. 37, pp. 1668-1675; published online Sep. 17, 2007(of record).*
Ebo et al., Cytometry Part B (Clinical Cytometry), vol. 64B, pp. 28-33; 2005 (of record).*
Ortolani et al., Allergy, vol. 53, Suppl. 46, pp. 58-61; 1998 (of record).*
Ebo Didier et al., Combined analysis of intracellular signalling and immunophenotype of human peripheral blood basophils by flow cytometry: a proof of concept. Clinical and Experimental Allergy 2007, vol. 37, pp. 1668-1675.
Aerts Nicolaas et al., Simultaneous Flow Cytometric Detection of Basophil Activation Marker CD63 and Intracellular Phosphorylated p38 Mitogen-Activated Protein Kinase in Birch Pollen Allergy. Cytometry Part B 2009, vol. 76B, pp. 8-17.

* cited by examiner

*Primary Examiner* — Soren Harward
*Assistant Examiner* — Paul D. Pyla
(74) *Attorney, Agent, or Firm* — McCarter & English LLP

(57) ABSTRACT

Methods are provided for determining a subject's susceptibility to an allergic reaction upon exposure to an offending allergen. Methods are also provided for determining and monitoring a subject's responsiveness to ongoing allergy treatment

5 Claims, 11 Drawing Sheets

Figure 1:
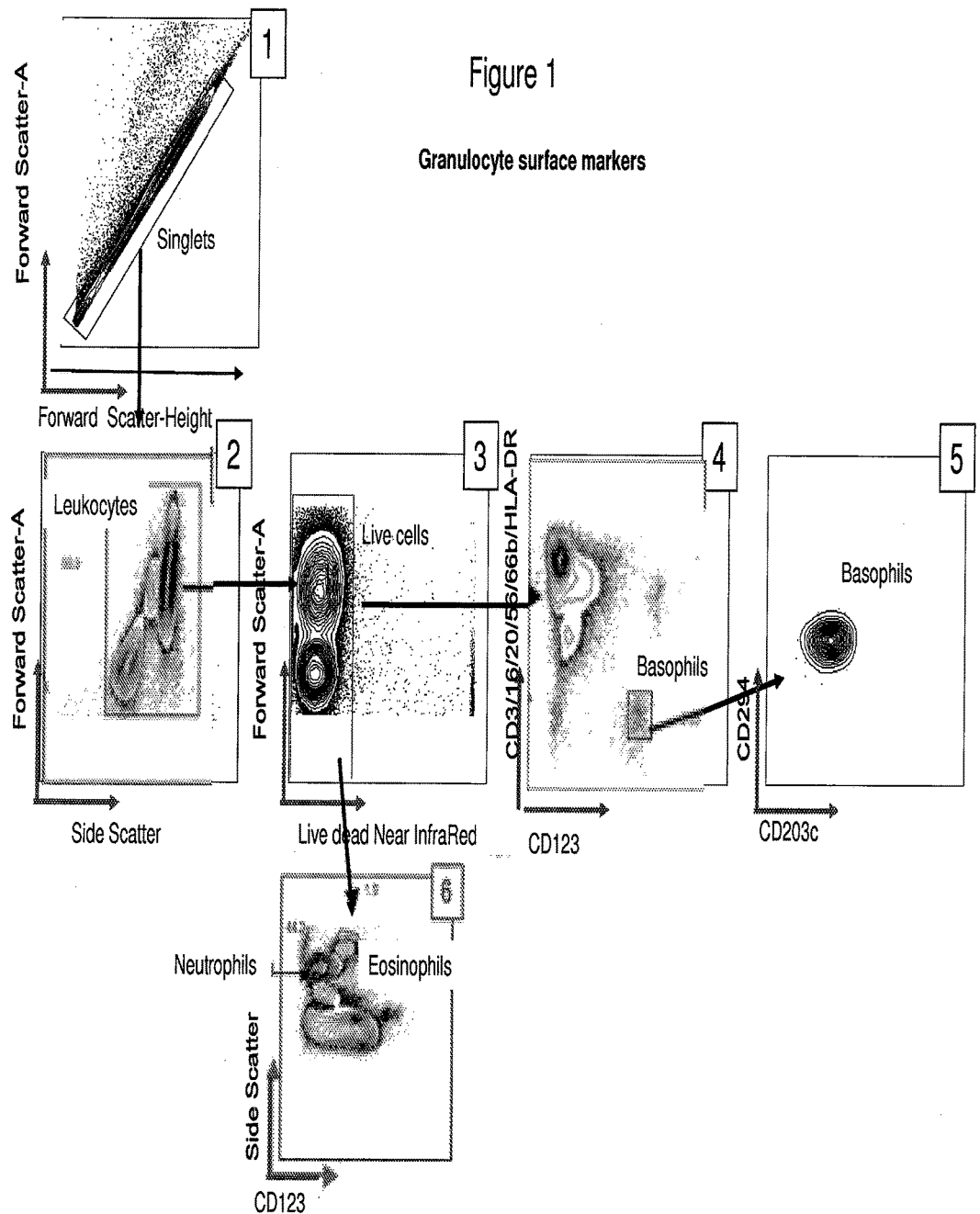

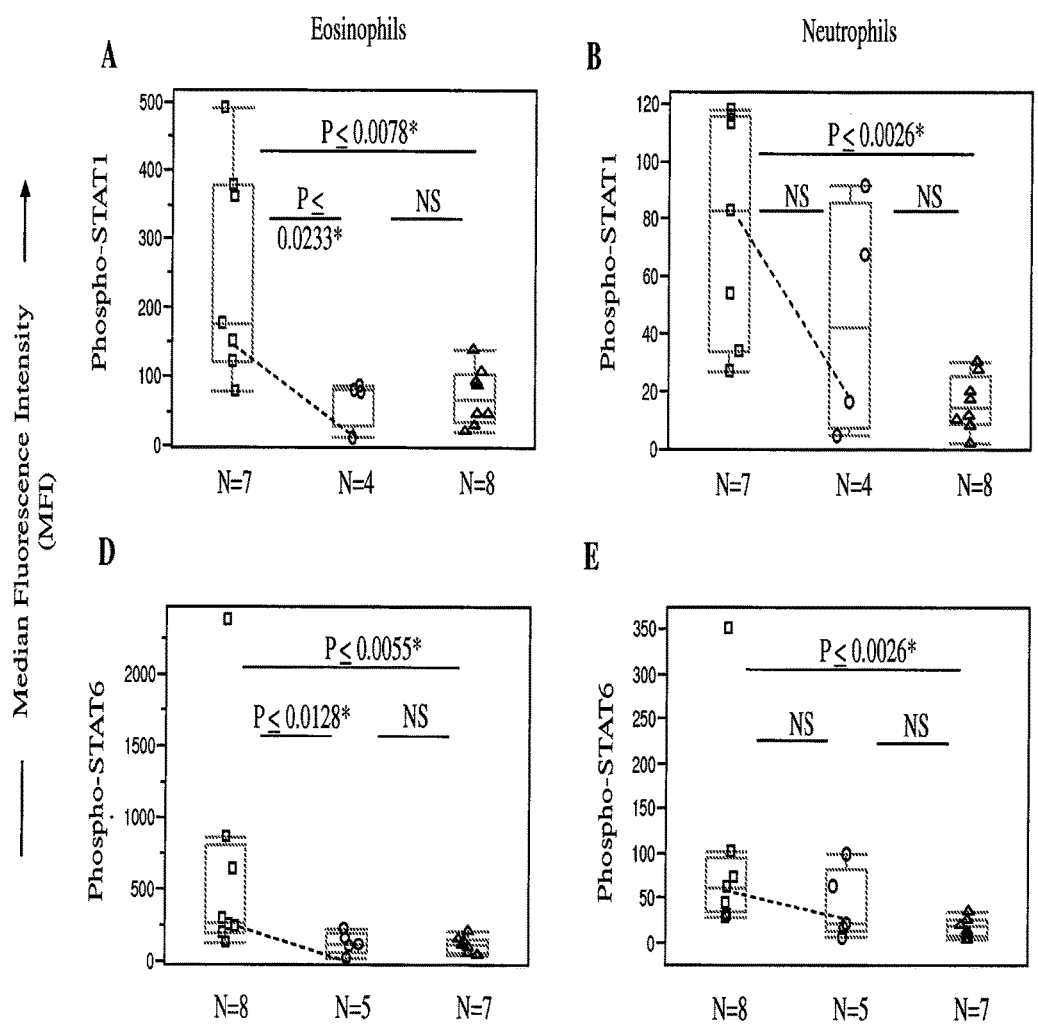
Figure 4, Panels A, B, D, E

Figure 4, Panels C, F
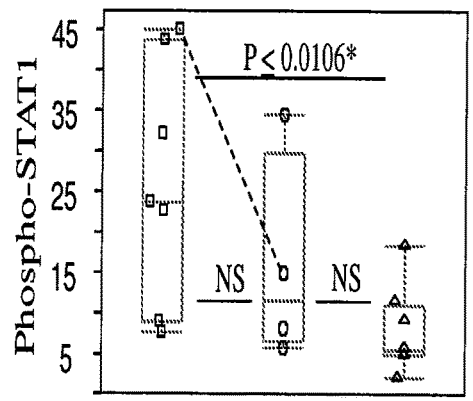
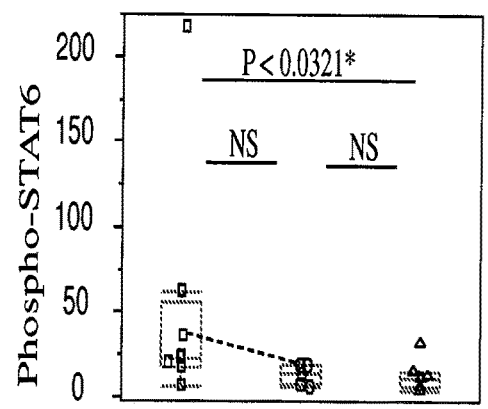

Figure 4, Panels G, H, I
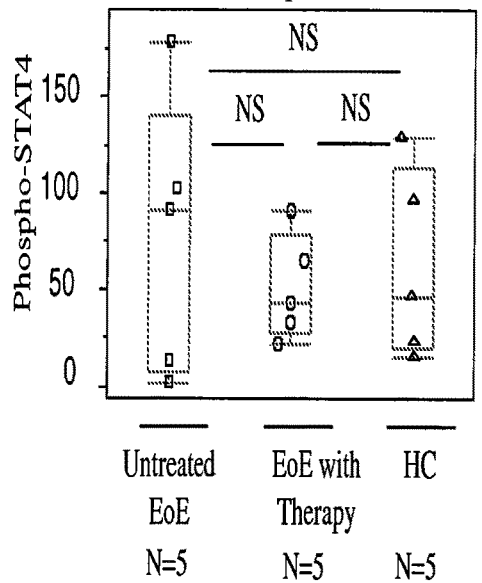
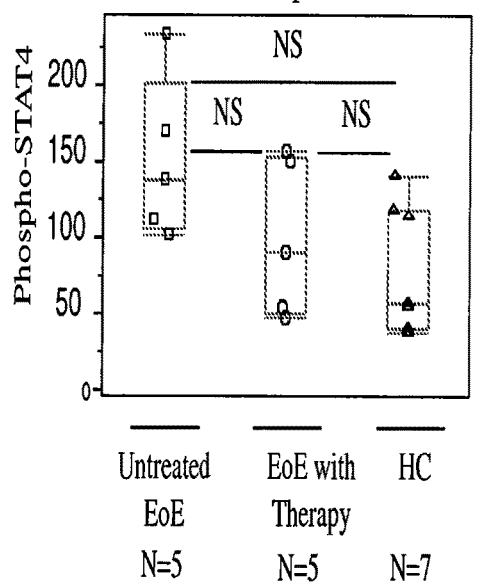
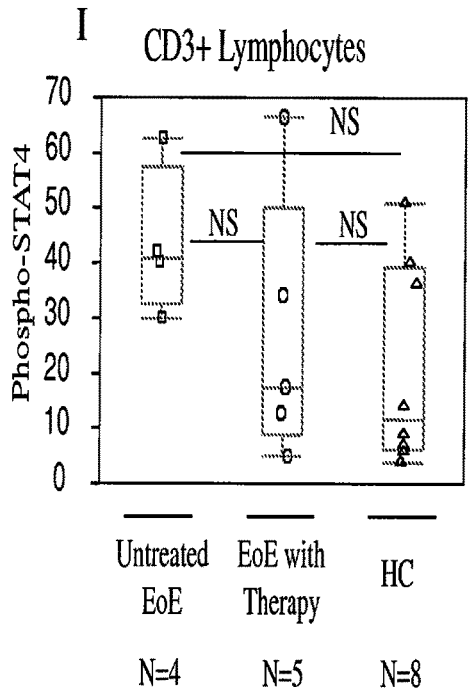

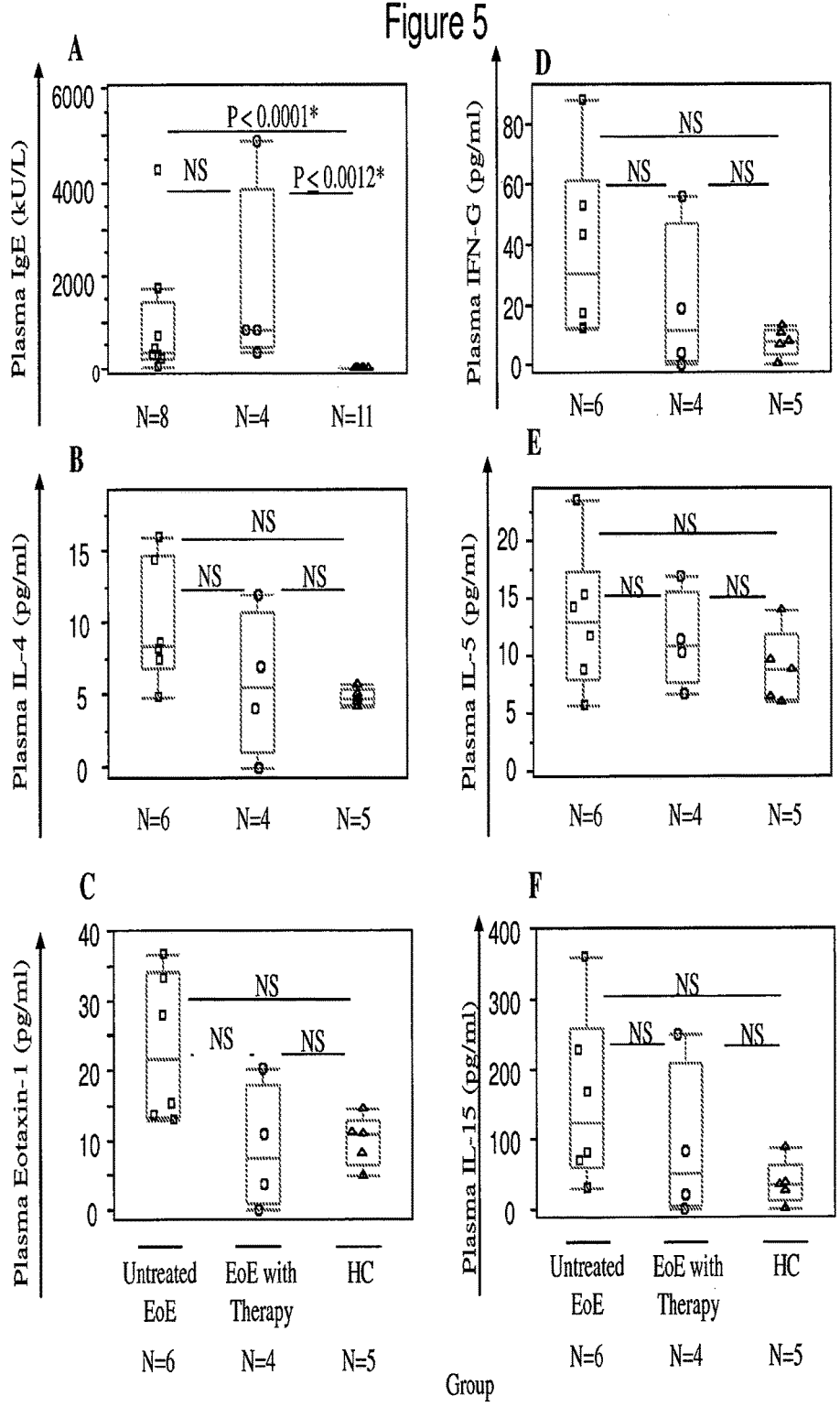

GRANULOCYTE-BASED METHODS FOR DETECTING AND MONITORING IMMUNE SYSTEM DISORDERS

RELATED APPLICATION

This application claims priority and other benefits from U.S. Provisional Patent Applications Ser. 61/144,152, filed Jan. 12, 2009, entitled "Rapid, safe and reliable granulocyte-based blood test for the detection of allergy to specific food, environmental, microbial, nanoparticle, metal and drug-related antigens in patients". Its entire content is specifically incorporated herein by reference.

TECHNICAL FIELD OF THE INVENTION

The present invention relates to methods for the detection and monitoring of immune system disorder, conditions or diseases.

BACKGROUND

The analysis of subpopulations of white blood cells (leukocytes) in blood or bone marrow is of particular interest for the evaluation of immune system disorders and immune system-related diseases, especially of allergic diseases. Granulocytes are a subpopulation of leukocytes and encompass neutrophils, eosinophils as well as basophils, which all differ in their staining characteristics and abundance in blood.

Neutrophils are the most abundant white blood cells in humans and account for approximately 70% of white blood cells, while basophils and eosinophils are much rarer, accounting for less than 1 percent and 1-6% of white blood cells, respectively.

Both basophils and eosinophils play important roles in Immunoglobulin E-mediated (IgE-mediated) immune responses including food allergies, severe asthma and responsiveness to environmental allergens. The basophil and/or eosinophil count often increases prior to the onset of symptoms and the activation state of basophils and eosinophils may correlate with the symptoms.

Allergies of diverse causes are on the rise particularly in developed countries as a consequence of heightened susceptibility towards aeroallergens, (heavy) metals, metal alloys, food allergens, xenobiotics, microbial allergens and more. The identification and quantitation of IgE antibodies is central in common tests to diagnose allergy; however, not all allergies are IgE-mediated.

Food allergy is a major public health problem that affects as many as 3-4% of adults and 6% of children in the United States. The incidence of allergic diseases and food allergies has increased 10-fold in developed countries in the last two decades. Currently used, first-line methods for identifying offending antigens are based on in-vivo as well as in-vitro allergen tests.

The in-vivo allergen testing is usually carried out as a skin test, which is typically uncomfortable for the patient, in particular for the pediatric patient, and often inconclusive. In-vitro allergen tests include radio-allergo sorbent test (RAST), immunoCAP and histamine liberation tests. These assays are blood-based, typically require several milliliters of blood and several days until the test results are available; in addition, none of these have proven reliable in terms of specificity and sensitivity.

If these first-line assays remain inconclusive, an in-vivo food challenge test is carried out in a double-blind, placebo-controlled fashion to determine the offending allergen. This test is not only difficult to administer, it is also very time-consuming and, most importantly, potentially highly dangerous since it can result in anaphylactic shock and even death, if treatment is not initiated quickly.

Taken together, the identification of an offending allergen is not always possible and not all allergies are IgE-mediated, rendering many common in-vitro and in-vivo tests inadequate for the specific and reliable determination of the causes of allergic reactions. Consequently, there is a great, currently unmet need for specific, sensitive, safe and rapid methods to determine a subject's susceptibility to possibly offending allergens of diverse origin.

SUMMARY

The present invention addresses the currently unmet need for specific, sensitive, safe and rapid methods to determine a subject's susceptibility to possibly offending allergens of diverse origin.

Embodiments of the present invention describe an ex vivo, blood-based method for determining a subject's susceptibility to an allergic reaction upon exposure to an offending allergen, wherein the subject has no known allergy to the allergen or known predisposition. The method is based on the monitoring and detection of intracellular signaling, e.g. phosphoepitopes, in live basophils, eosinophils and/or other granulocytes from the subject, following stimulation to the offending allergen. The method is also based on the detection of intracellular signaling, e.g. phosphoepitopes, in live basophils, eosinophils and/or other granulocytes at baseline level (without any stimulation) ex vivo.

Diseases and disorders where this method will be useful are food allergy, airborne allergy, drug-induced allergy mediated through the ingestion, inhalation, injection or skin exposure to a xenobiotic, anaphylaxis, asthma and other immune disorders caused by microbes or contact with (heavy) metals or metal alloys.

Particular embodiments of the invention use very small volumes of blood (100 µl or less per assay) and so are also suitable for studies in all type of subjects (e.g. infants, children, healthy and sick individuals).

INCORPORATION BY REFERENCE

All publications and patent applications mentioned in this specification are herein incorporated by reference to the same extent as if each individual publication or patent application was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 1 illustrates an example of granulocyte (neutrophil, eosinophil and basophil) detection from less than one drop of blood (without any stimulation). 1) We gated the single cells based on the forward scatter area and the forward scatter area height; 2) we selected leukocytes based on forward scatter area and side scatter; 3) we excluded compromised cells with Live/Dead viability marker; and 4) then, we excluded the B, T, NK cells, NK T cells, dentritic cells, monocytes and selected the neutrophils, or the eosinophils or the basophils from the same stained sample (neutrophils are defined as side scatter high and CD123 negative: eosinophils are defined as CD123 high and side scatter high: basophils are defined as: negative for live dead, CD3, CD16, CD20, CD56, CD66b and HLA-Dr and positive for CD123, CD294 and CD203c). This assay can identify simultaneously and specifically each subset of granulocyte (neutrophils, eosinophils, basophils) with only 5 channels (2 scatter channels and three fluorescent channels measuring a viability marker, a set of markers for various populations and a positive marker for basophils).

Figure 2:
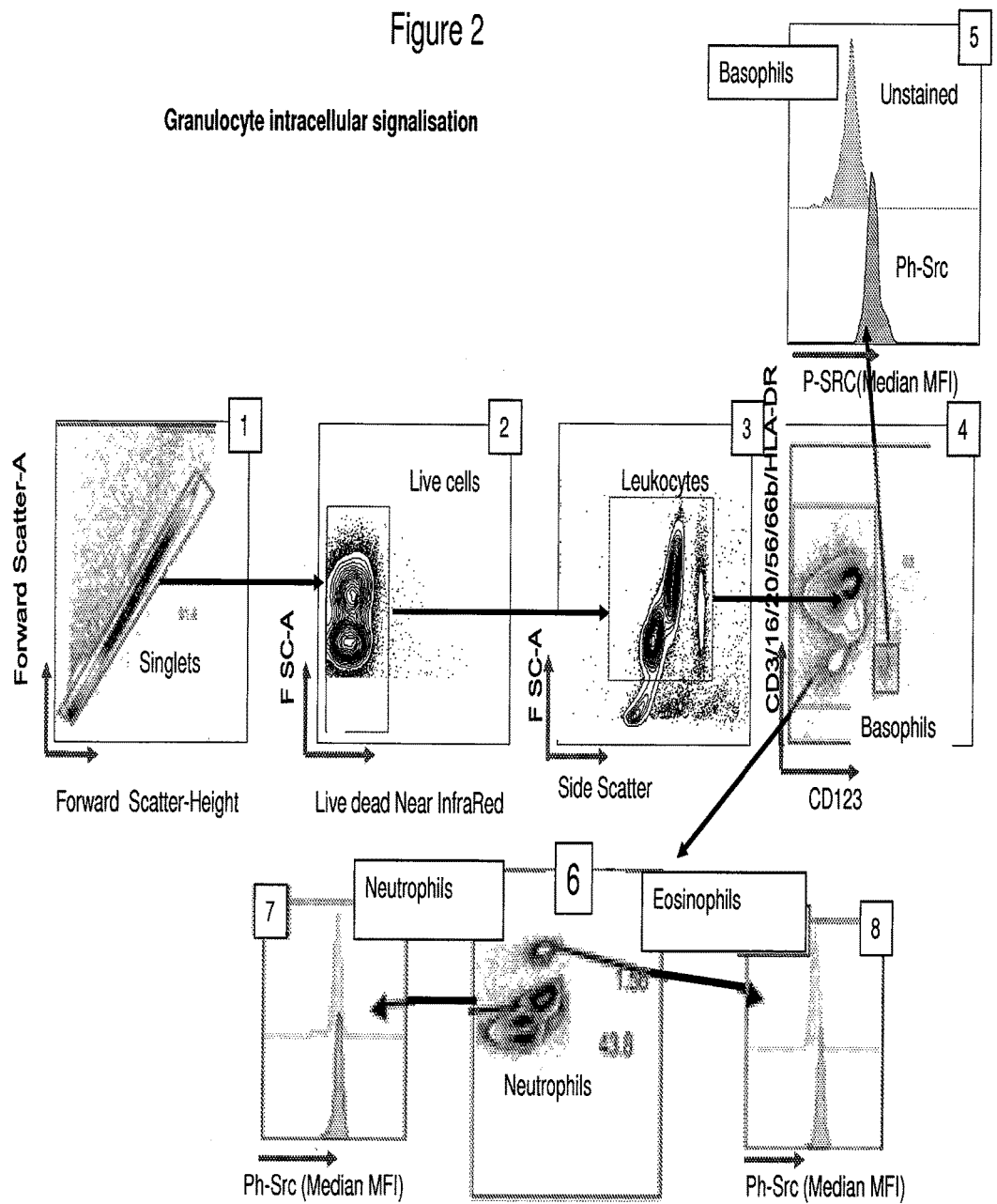

FIG. 2 illustrates an example of intracellular signalisation detection in live granulocytes (neutrophils, eosinophils and basophils) from whole blood (without any stimulation). 1) We gated neutrophils, eosinophils as illustrated above, Basophils were defined as negative for live dead marker, CD3, CD16, CD19 or CD20, CD56, CD66b and positive for CD123 2) As an example, a phospho-SRC signal was measured simultaneously in each subset.

Figure 3:
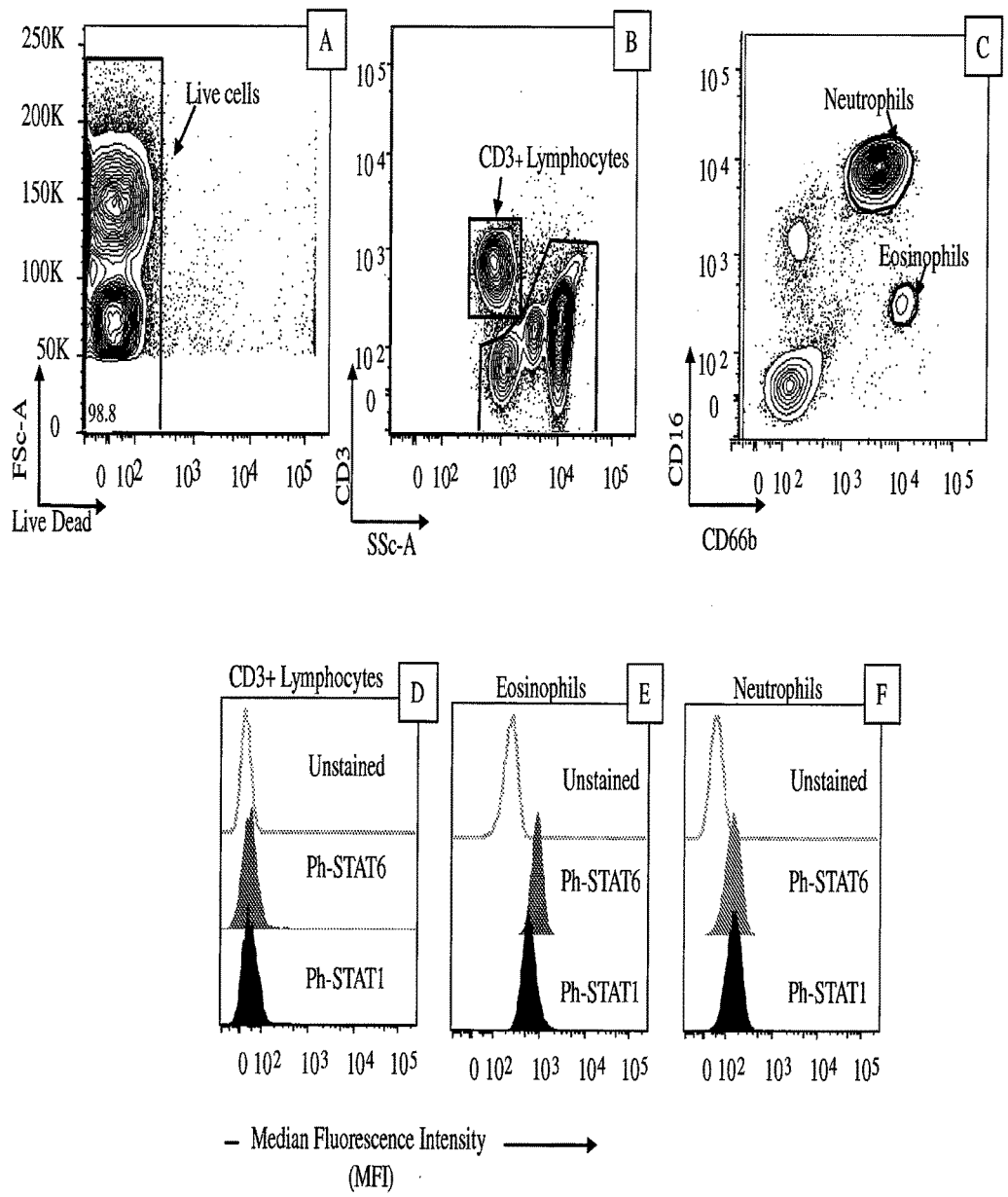

FIG. 3 illustrates the identification of eosinophils, neutrophils, and CD3+ lymphocytes from less than one drop of whole blood. A: Viable cells are identified from whole blood using a fixable Live/Dead probe. B: CD3+ lymphocytes are identified based on positive staining with anti-CD3 antibody. C: Neutrophils and eosinophils are identified as being CD16-positive, CD66b-positive or CD16-intermediate, CD66b-positive, respectively. Median fluorescence intensities of phospho-STAT1 and phospho-STAT6 are measured in CD3+ lymphocyte (D), eosinophil (E), and neutrophil (F) subsets.

FIG. 4 shows levels of intracellular phospho-STATs in blood eosinophils, neutrophils, and CD3+ lymphocytes. A-F: Phospho-STAT1 and 6 levels in eosinophils, neutrophils, and CD3+ lymphocytes help to distinguish untreated EoE from HC subjects. A, D: Phospho-STAT1 and 6 levels in eosinophils also help to distinguish untreated EoE from EoE subjects with therapy. G-I: Phospho-STAT4 shows no significant differences. Broken lines connect points for subject #1 before and during therapy. NS, not significant.

FIG. 5 illustrates the analysis of disease indicators in plasma. Plasma molecules associated with STAT1 and/or STAT6 signaling or with EoE pathogenesis are measured using Luminex Technology. A: Plasma IgE levels are significantly higher for EoE subjects, both with and without therapy, compared with HC subjects. B-F: No significant differences are observed for plasma levels of IL-4, eotaxin-1, IFN-γ, IL-5, and IL-15. NS, not significant.

Figure 6:
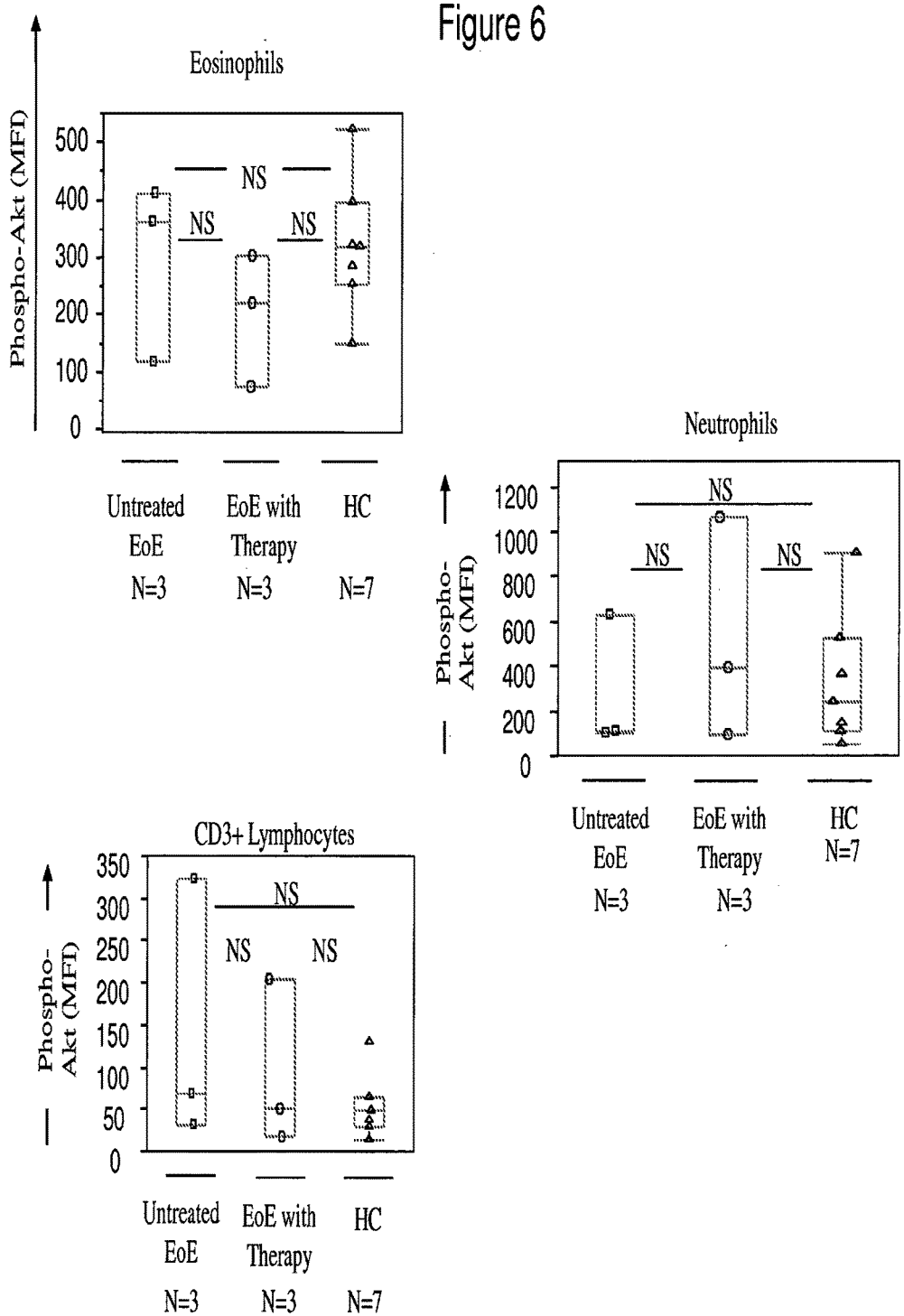

FIG. 6 illustrates the expression level of intracellular phospho-Akt in live blood eosinophils, neutrophils and CD3+ lymphocytes. Levels of intracellular phospho-Akt were measured in blood eosinophils, neutrophils, and CD3+ lymphocytes. No significant differences were observed between untreated EoE subjects, EoE subjects with therapy or healthy controls. NS, not significant.

Figure 7:
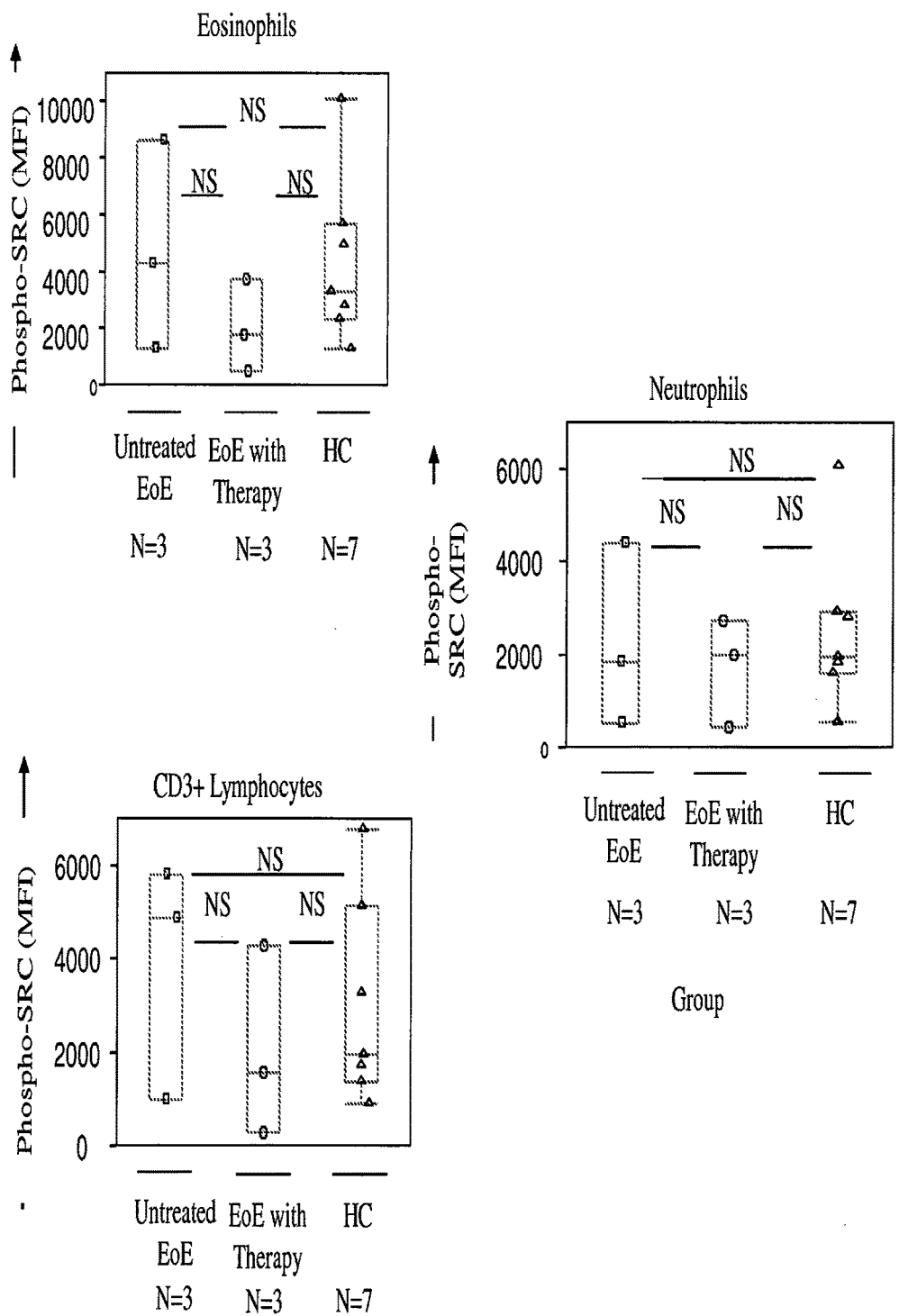

FIG. 7 illustrates the expression level phospho-SRc in live blood eosinophils, neutrophils, and CD3+ lymphocytes. Levels of intracellular phospho-SRc were measured in live blood eosinophils, neutrophils and CD3+ lymphocytes. No significant differences were observed between untreated EoE subjects, EoE subjects with therapy or healthy controls. NS, not significant.

Figure 8:
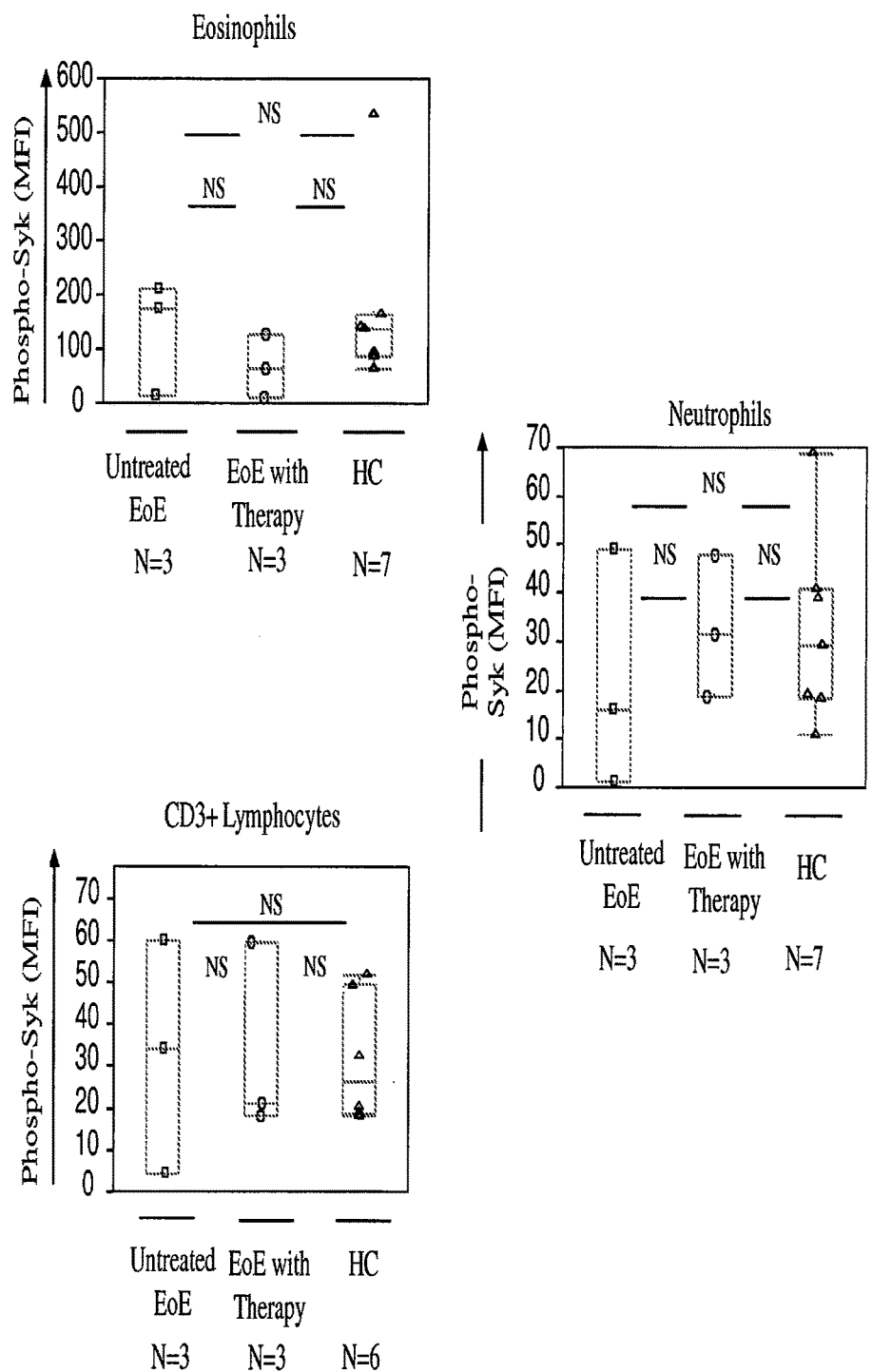

FIG. 8 illustrates the expression level phospho-Syk in live blood eosinophils, neutrophils, and CD3+ lymphocytes. Levels of intracellular phospho-Syk were measured in live blood eosinophils, neutrophils and CD3+ lymphocytes. No significant differences were observed between untreated EoE subjects, EoE subjects with therapy or healthy controls. NS, not significant.

Figure 9:
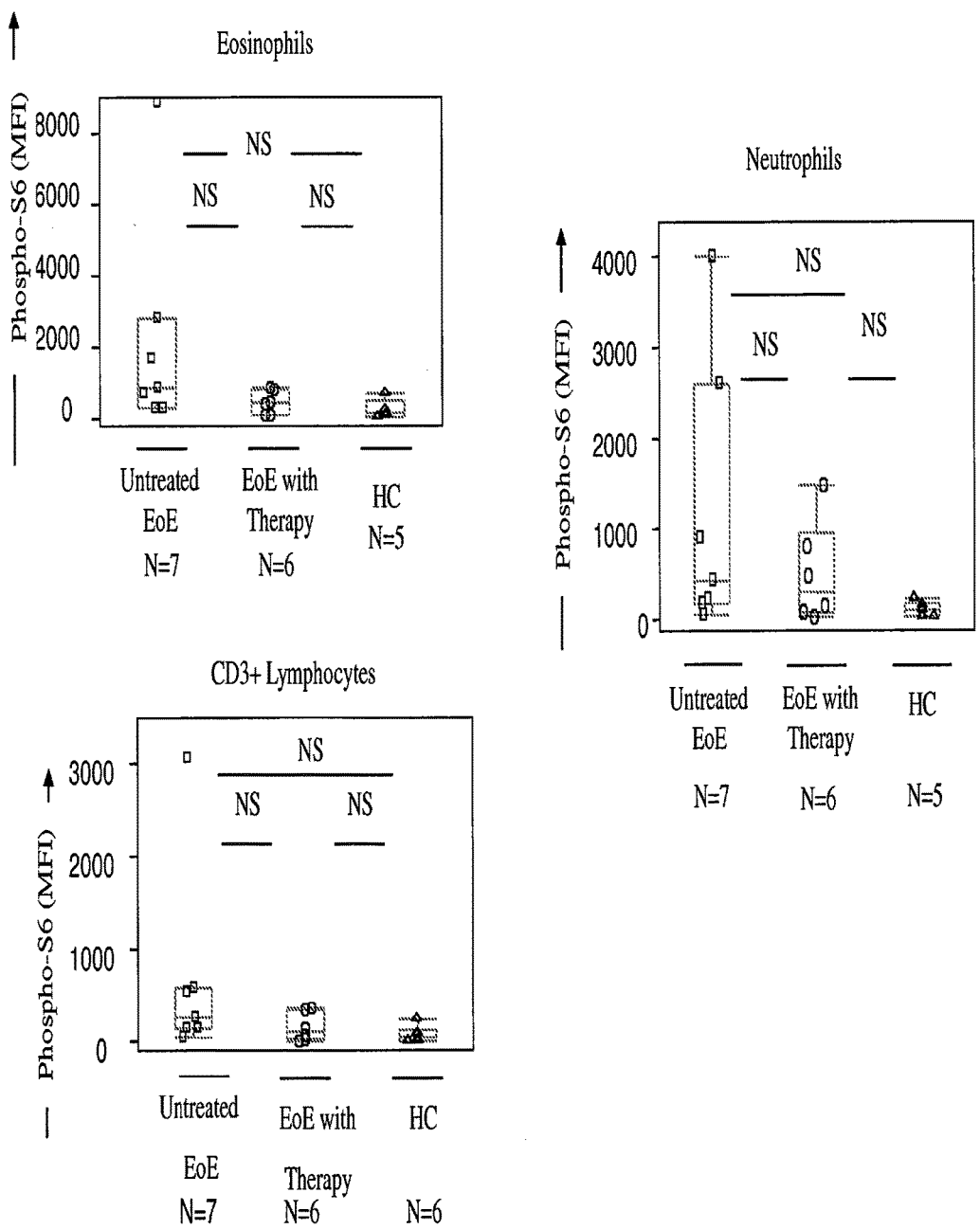

FIG. 9 illustrates the expression level of phospho-S6 ribosomal protein in live blood eosinophils, neutrophils, and CD3+ lymphocytes. Levels of intracellular phospho-S6 ribosomal protein were measured in live blood eosinophils, neutrophils and CD3+ lymphocytes. No significant differences were observed between untreated EoE subjects, EoE subjects with therapy or healthy controls. NS, not significant.

DEFINITIONS

The practice of the present invention may employ conventional techniques of chemistry, molecular biology, recombinant DNA, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable.

The term "subject", "mammalian subject", "individual" or "patient" are used interchangeably herein to refer to a member of a species of mammalian origin, including but not limited to a human, mouse, rat, cat, goat, sheep, horse, hamster, ferret, pig, dog, guinea pig, rabbit or primate, adult or not yet adult.

The terms "allergic response" and "allergy" are used interchangeably herein to describe an abnormal reaction of the body to a previously encountered allergen introduced by inhalation, ingestion or skin contact. The use of these terms also includes clinically adverse reactions to environmental allergens which reflect the expression of acquired immunologic responsiveness involving allergen-specific antibodies and/or T cells. These terms also include adverse immunologic responses that are associated with the production of allergen-specific IgE.

The term "allergen", as used herein, refers to any substance that induces an allergy in a susceptible subject. The use of the term "allergen" includes any antigens that elicit a specific IgE response. Allergens may have little or no intrinsic toxicity by themselves, but cause a pathological condition due to their ability to elicit an IgE-associated immune response, and, upon subsequent exposure, due to their ability to elicit IgE- and/or T cell-dependent hypersensitivity reactions. Common allergens include but are not limited to pollen, grasses, dust, as well as foods, including, but not limited to, nuts, milk, eggs, shell fish, venoms, and various drugs.

The term "allergic diseases", as used herein, refers to a group of clinically manifested disorders in which immune responses, typically directed against otherwise innocuous environmental allergens, are thought to have a pathogenetic role. Allergic diseases include, but are not limited to, hay fever, allergic asthma, allergic contact dermatitis, and clinical disorders in which IgE-associated immune responses are thought to play a role.

The term "activation", as used herein, refers to a physiological condition upon exposure to a substance, allergen, drug, protein, chemical, or other stimulus, or upon removal of a substance, allergen, drug, protein, chemical or other stimulus.

The term "activation marker", as used herein, refers to an intracellular signaling marker which is highly associated with a particular cell and which is selectively and reproducibly upregulated during a physiological condition. The physiological condition may be the result of an exposure to a substance, allergen, drug, protein, chemical, or other stimulus, or maybe the result of removal of a substance, allergen, drug, protein, chemical or other stimulus.

The term "active" or "activated", as used herein, refers to having a biological or physiological effect that differs from the native biological, physiological, or wildtype, state.

The term "nonactivated", as used herein, refers to a native biological, physiological, or wildtype, state.

The term "activatable", as used herein, refers to having potential to become biologically or physiologically active.

The term "normal", as used herein, refers to a standard, model, median or average of a large group. "Abnormal", as used herein, refers to a deviation of the standard, model, median or average of a large group.

The term "antigen", as used herein, refers to any substance that can stimulate the production of antibodies and can combine specifically with them. The term "antigenic determinant" or "epitope", as used herein, refers to an antigenic site on a molecule.

The term "biological sample", as used herein, refers to a sample consisting of or containing blood, serum, plasma, lymph fluid, amniotic fluid, saliva, cerebro-spinal fluid, lacrimal fluid, mucus, urine, sputum, or sweat.

The term "drop", as used herein, refers to a small quantity of liquid or liquid globule that is produced, or falls, in a more or less spherical mass.

The term "cell surface marker", as used herein, refers to an antigenic determinant or epitope found on the surface of a specific type of cell. Cell surface markers can facilitate the characterization of a cell type, its identification, and eventually its isolation. Cell sorting techniques are based on cellular biomarkers where one or more cell surface markers are used for either positive or negative selection, i.e., for inclusion or exclusion, from a cell population.

The term "phosphoepitope", as used herein, refers to a phosphorylated protein on a cell surface or inside a cell. A comparison of phosphoepitopes can be used to determine the activation status of a cell or cell population as the measurement of phosphorylation of signaling intermediates may allow for association of network topologies with diseases states. For example, transduction signaling cascades involve transmembrane receptors that bind to a specific extracellular ligand, such as a hormone or a cytokine. This binding initiates the transduction of a signal by a cascade of intracellular enzymal events that ultimately results in degranulation, apoptosis, proliferation, migration, organization of the assembling of ribosomes, and/or gene transcription. These transduction cascades often proceed by sequentially adding or removing phosphate residues via phosphorylation or dephosphorylation to a series of enzymes in the cascade. Within the transduction signaling cascades, four components are important: (1) the transmembrane receptor and its specific ligand; (2) the kinases, i.e. phosphorylating enzymes that up- or down-regulate the activity of cascade enzymes; (3) phosphatases, i.e. dephosphorylating enzymes; and (4) the final acceptor of the cascade which performs the function(s) that the cascade triggers.

The term "cytometry", as used herein, refers to a process in which physical and/or chemical characteristics of single cells, or by extension, of other biological or nonbiological particles in roughly the same size or stage, are measured. In flow cytometry, the measurements are made as the cells or particles pass through the measuring apparatus (flow cytometer) in a fluid stream. A cell sorter, or flow sorter, is a flow cytometer that uses electrical and/or mechanical means to divert and collect cells (or other small particles) with measured characteristis that fall within a user-selected range of values.

The term "contacting", as used herein, refers to a state of touching or immediate or local proximity.

The term "disease" or "disorder", as used herein, refers to an impairment of health or a condition of abnormal functioning.

The term "drug", as used herein, refers to a therapeutic agent or any substance, other than food, used in prevention, diagnosis, alleviation, treatment or cure of disease.

The term "differential label", as used herein, generally refers to a stain, dye, marker, or antibody used to characterize or contrast structures, components or proteins of a single cell or organism.

The term "labeling", as used herein, refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The term "stain", as used herein, refers to a composition of one or more dyes or pigments used to make differentiable a structure, a material, a cell, a cell component, a membrane, a granule, a nucleus, a cell surface receptor, a peptide, a microorganism, a nucleic acid, a protein or a tissue.

The term "susceptible", as used herein, refers to a member of a population at risk. The term is inclusive of a subject having a medical history of a previous allergic reaction to at least one allergen and at risk of mounting an allergic reaction to a different antigen.

The term "anaphylactic shock", as used herein, refers to a sudden, severe allergic reaction typically characterized by a sharp drop in blood pressure, urticaria, and breathing difficulties that are caused by exposure to a foreign substance after a preliminary or sensitizing exposure.

The term "expression", as used herein, refers to the action of a gene in the production or a protein or phenotype. "Level of expression" refers to the degree to which a particular gene produces its effect(s) in an organism.

The term "dye", as used herein, (also referred to as "fluorochrome" or "fluorophore") refers to a component of a molecule which causes the molecule to be fluorescent. The component is a functional group in the molecule that absorbs energy of a specific wavelength and re-emits energy at a different, but equally specific wavelength. The amount and wavelength of the emitted energy depend on both the dye and the chemical environment of the dye.

The term "fluorescence", as used herein, refers to the result of a three-state process that occurs in certain molecules, generally referred to as "fluorophores" or "fluorescent dyes", when a molecule or nanostructure relaxes to its base level state after being electrically excited. Stage 1 involves the excitation of a fluorophore through the absorption of light energy. Stage 2 involves a transient excited lifetime with some loss of energy. Stage 3 involves the return of the fluorophore to its base level state accompanied by the emission of light.

The term "fluorescent-activated cell sorting" (also referred to as "FACS"), as used herein, refers to a method for sorting a heterogeneous mixture of biological cells into one or more containers, one cell at a time, based upon the specific light scattering and fluorescent characteristics of each cell.

The term "isolated", as used herein, refers to placing, setting apart, or obtaining a protein, molecule, substance, nucleic acid, peptide, cell or particle, in a form essentially free from contaminants or other materials with which it is commonly associated.

The term "stimulation", as used herein, describes the addition of a defined amount of test allergens/antigens to a blood sample from patients with suspected allergies and subsequent incubation at controlled temperature.

The term "venipuncture", as used herein, refers to the process of obtaining intravenous access for the purpose of intravenous therapy or obtaining a sample of venous blood.

The term "whole blood", as used herein, refers to generally unprocessed or unmodified collected blood containing all of its components, such as red blood cells, white blood cells, platelets and plasma. The term "whole blood" is inclusive of any anticoagulant that may be combined with the blood upon collection.

DETAILED DESCRIPTION

Embodiments of the present invention describe an ex vivo, whole blood-based method for determining a subject's susceptibility to an allergic reaction upon exposure to an offending allergen. The method is based on the monitoring and detection of intracellular signaling, e.g. phospho-epitopes, in live basophils, eosinophils and/or neutrophils from the subject, at baseline level (without any stimulation) and/or following stimulation by the offending allergen.

Particular embodiments of the present invention determine the granulocyte response to the binding of the allergen to allergen-specific IgE or other relevant Ig in whole blood, without prior isolation of granulocytes. There is no need to pre-isolate the granulocytes, since their activation is detected by flow cytometric assays that enable functional isolation and detection of specific signaling in granulocytes in small amounts of appropriately stimulated whole blood.

According to one aspect, the present invention provides a method for determining a subject's response to an allergen challenge in a whole blood sample obtained from a subject that might be allergic to that allergen. The method comprises the steps of collecting a whole blood sample from the subject, contacting the white blood cells from the whole blood sample with an allergen, fractionating the whole blood sample by flow cytometry to separate basophilic, neutrophilic and eosinophilic granulocytes from each other as described in U.S. Ser. No. 61/110,283 and U.S. Ser. No. 12/610,940, which entirely are incorporated by reference, assessing the level of expression of at least one intracellular signaling marker that is characteristic to the basophilic, neutrophilic or eosinophilic granulocytes and correlating the expression of the at least one intracellular signaling marker that is characteristic to the basophilic, neutrophilic or eosinophilic granulocytes with the subject's response to the allergen challenge.

Immune System Disorders and Immune-System Related Diseases Allergy

Allergy

Allergy is a disorder of the immune system and is characterized by the occurrence of allergic reactions to normally harmless environmental substances known as allergens; these reactions are acquired, predictable, and rapid. Allergies are caused by allergens, which may be present in a wide variety of sources, including but not limited to pollens or other plant components, dust, moulds or fungi, foods, additives, latex, transfusion reactions, animal or bird danders, insect venoms, radiocontrast medium, medications or chemicals. Common allergic reactions include eczema, hives, hay fever, asthma, food allergies and reactions to venoms. Mild allergies like hay fever are highly prevalent in the human population and cause symptoms such as allergic conjunctivitis, itchiness, and runny nose. In some people, severe allergies to environmental or dietary allergens or to medication may result in life-threatening anaphylactic reactions and potentially death, if left untreated. Allergic reactions can occur in three distinct patterns: a) an early phase reaction or acute response, b) late phase reactions and c) potentially chronic allergic inflammation. The early phase of the allergic reaction typically occurs within minutes, or even seconds, following a first allergen exposure and is also commonly referred to as the immediate allergic reaction. In the early stages of allergy, a hypersensitivity reaction against an allergen, encountered for the first time, cause a response in Th2 cells, which are a subset of T cells that produce the cytokine interleukin-4 (IL-4). The Th2 cells interact with B cells (lymphocytes that produce antibodies against antigens) and, coupled with the effects of IL-4, stimulate the B cells to begin production and secretion of Immunoglobulin E (IgE).

IgE plays an important role in allergies and allergic reactions. Upon introduction of an allergen, B cells of the respective subject produce large amounts of IgE. The IgE elicits an immune response by binding onto receptors found on basophils and mast cells. When activated, these cells release chemical mediators such as histamine and cytokines that cause the characteristic symptoms of allergy.

Immunoglobulin G (IgG) is an abundant immunoglobulin in humans that protects the individual from pathogens such as viruses, bacteria, and fungi. Upon introduction of a pathogen, IgG binds to the pathogen, allowing for various defense mechanisms such complement activation, opsonization for phagocytosis, and neutralization of pathogen toxins. IgG also plays a role in food allergies. In contrast to IgE-mediated allergic reactions to food, whose symptoms appear rapidly, IgG-mediated allergic reactions to food have a delayed onset. IgG can be divided into various subclasses based on their effector functions.

The secreted IgE circulates in the blood and binds to the high affinity IgE receptor (FcεRI) on the surface of mast cells and basophils, both of which are involved in the acute inflammatory response. At this state, the IgE-coated cells are sensitized to the allergen. Mast cells are very similar to basophils; however, current evidence suggests that they are generated by different precursor cells in the bone marrow.

If later exposure to the same allergen occurs, the allergen can bind to the IgE molecules held on the surface of the mast cells or basophils. Cross-linking of the IgE and high affinity IgE receptors occurs when more than one IgE-receptor complex interacts with the same allergenic molecule, and activates the sensitized cell. Subsequently, these activated mast cells and basophils undergo the process of degranulation during which they release histamine and other inflammatory chemical mediators, such as cytokines, interleukins and prostaglandins, from their granules into the surrounding tissue causing several systemic effects, such as vasodilation, mucous secretion, nerve stimulation, and smooth muscle contraction. This may result in rhinorrhea, itchiness, dyspnea, or anaphylaxis. Depending on the individual subject, allergen and mode of introduction of the allergen, the symptoms may be system-wide or localized to a particular body system.

After the chemical mediators of the acute response subside, late phase responses may occur. Tissue may become red and swollen due, initiated by the release of cytokines from mast cells and basophils, to the migration of other white blood cells such as neutrophils, lymphocytes, eosinophils and macrophages to the initial site. The reaction can occur between 2 to 24 hours following repeated contact with an offending allergen. Chronic allergic inflammations can persist for days to years. Once a subject is sensitized, i.e. has been exposed repeatedly to an offending allergen, a range of tissue responses might ensue, depending on such factors as the route, frequency and extent of allergen exposure, and on whether the allergen exposure represents a single transient occasion, results in the persistence of the allergen, or occurs seasonally, e.g. as in the case of hay fever, or in some other repetitive fashion. Tissue responses may also be affected by the genetic background of the subject and by diverse non-genetic factors, such as a concurrent infection, which might modify the subject's response to an allergen.

Allergy Treatments

Treatments for allergies include allergen avoidance, local or internal use of anti-histamines, local or internal use of corticosteroids, immunotherapy to (gradually) desensitize the response to allergen, and targeted pharmacological intervention.

Monitoring of Allergy Treatment Success

Consistent allergen avoidance would be ideal, but is not practical or feasible. The quality of life of a subject that is susceptible to one or more offending allergens is greatly affected by the quality of allergy treatment management that he/she receives. It is important to monitor a subject receiving allergy treatment to determine whether and, if yes, how well the disease is kept under control, whether the subject is compliant with therapy and how well the subject responds to the chosen therapy so that the allergy/allergic disease does not exacerbate and escalates in a major, life-threatening allergic reaction/anaphylaxis. Successful therapeutic monitoring will at last not only improve the subject's quality of life, it will also reduce the subject's state, duration and frequency of morbidity and need for urgent medical intervention.

Allergic Diseases

Allergic diseases are a group of hypersensitivity disorders that may be associated with the production of specific IgE to environmental allergens and involve IgE-mediated reactions.

Anaphylactic Shock or Anaphylaxis

Anaphylaxis is an acute, systemic hypersensitivity response to an allergen, which typically involves multiple organ systems and which, if left untreated, rapidly leads to death. Anaphylaxis can occur IgE-dependent as well as IgE-independent.

Allergic Conjunctivitis

Allergic eye disease primarily affects the conjunctiva. The signs and symptoms include itching, tearing, conjunctival edema, hyperemia, watery discharge, burning, and photophobia. Eyelid edema is also common. Symptoms are usually bilateral; however, one eye can be affected more than the other. The diagnosis of allergic conjunctivitis is usually made clinically.

Allergic Rhinitis

Allergic rhinitis (hay fever) is one of the most prevalent allergic diseases. It generally is believed that symptoms, which include sneezing, nasal congestion and itching, and rhinorrhea primarily reflect the IgE-dependent release of mediators by effector cells in response to aeroallergens. Accordingly, symptoms may be seasonal, correlating with the presence of the offending grass, weed or tree pollens, or mold spores, or year-round in the presence of dust mites and animal dander. Typically, symptoms develop rapidly upon exposure to allergen. Nasal tissues usually exhibit marked infiltration with eosinophils and basophils.

Asthma

Asthma is characterized by a predisposition to chronic inflammation of the lungs in which the airways (bronchi) are reversibly narrowed. In human allergic asthma IgE-dependent mast cell activation seems to contribute to acute allergen-induced bronchoconstriction, where the airways in the lungs are narrowed due to tightening of surrounding smooth muscles. IgE can directly or indirectly upregulate the expression of high affinity IgE receptors on basophils and mast cells, and, by binding to these receptors, prime the cells to release increased amounts of key mediators, such as histamine, IL-4 and other cytokines.

Allergic Contact Dermatitis

Allergic contact dermatitis, a type of eczema, is an inflammatory, chronically relapsing, non-contagious and pruritic skin disease. The skin of a patient with allergic contact dermatitis reacts overly sensitive to irritants, food, and environmental allergens and becomes red, flaky and very itchy. It also becomes vulnerable to surface infections caused by bacteria. Common allergens that can cause an allergic contact dermatitis include a) nickel (nickel sulfate hexahydrate), which is a metal alloy that is frequently encountered in jewelry and clasps or buttons on clothing; b) gold (gold sodium thiosulfate), a precious metal often found in jewelry; c) formaldehyde, which is contained as preservative in household cleaning products or paints; d) thiomerosal, a mercury preservative used in local antiseptics and in vaccines.

Food Allergy and/or Additives

A food allergy is an adverse immune response to a food protein. The food protein triggering the allergic response is termed a food allergen; common food allergens are shellfish, peanuts, tree nuts, fish, milk, eggs, fresh fruits such as strawberries, mango, banana, apple. Immunoglobulin-E (IgE)-mediated food allergies are classified as type-I immediate hypersensitivity reactions. These allergic reactions have an acute onset (from seconds to one hour) and the accompanying symptoms may include angioedema (soft tissue swelling of the eyelids, face, lips, tongue, larynx and trachea); hives; itching of the mouth, throat, eyes, skin; gastrointestinal symptoms such as nausea, vomiting, diarrhea, stomach cramps, or abdominal pain; rhinorrhea or nasal congestion; wheezing, shortness of breath, or difficulty swallowing; and even anaphylaxis, a severe, whole-body allergic reaction that can result in death.

Eosinophilic Esophagitis

Eosinophilic esophagitis (EoE) is part of a heterogeneous group of eosinophil-associated gastrointestinal disorders that is characterized by high numbers of eosinophils infiltrating into the esophagus. While the incidence of EoE is increasing, precise mechanisms of this disease remain largely unknown, though EoE seems to be associated with allergy. Currently, esophagogastroduodenoscopy (EGD) and histological examination of esophageal biopsies are required for the diagnosis of EoE, and repeated procedures are often employed for the assessment of response to therapy. Current treatments rely on avoidance of specific food and airborne allergens in atopic patients, anti-inflammatory drugs such as glucocorticoids, or experimental drugs, such as mepolizumab. The need for less invasive procedures to diagnose and monitor EoE remains.

Autoimmune Diseases

Auto-immune diseases are conditions in which a patient's body fails to recognize its own constituent parts as "self", resulting in an immune response against its own cells and tissues. Many different parts of the body can be affected by auto-immune diseases, including nerves, tissues, organs, and muscles.

Anaphylaxis

Anaphylaxis is defined as a serious allergic reaction that is rapid in onset and may cause death. The diagnosis of anaphylaxis is clinical and based primarily upon clinical symptoms and signs, as well as a detailed description of the acute episode, including antecedent activities and events. Anaphylaxis is a much broader syndrome than "anaphylactic shock" however, and the goal of therapy should be early recognition and treatment with epinephrine to prevent progression to life-threatening symptoms, including shock. Recognition of the variable and atypical presentations of anaphylaxis is therefore critical to providing effective therapy in the form of epinephrine, as well as reducing overreliance on less-effective medications, such as antihistamines and glucocorticoids.

Urticaria

Urticaria, or hives, is a common disorder affecting up to 25 percent of the population. The usual urticarial lesion is an intensely pruritic, circumscribed, raised, erythematous plaque, often with central pallor. Individual lesions may enlarge and coalesce with other lesions, and then typically will disappear over a few hours without leaving residual marks on the skin unless there is damage from scratching.

Allergic Angioedema

Acute allergic angioedema typically occurs within minutes to a few hours following exposure to foods, drugs, latex, or the stings of various insects. Urticaria is commonly present in this setting. It is most often seen in patients with other allergic conditions, such as atopic dermatitis, allergic rhinitis, and asthma. This type of angioedema is dependent upon the presence of IgE molecules specific to proteins in the causative agent. These specific IgE molecules bind to the patient's mast cells and trigger the reaction upon re-exposure to the antigen. Skin testing or in vitro immunoassays for specific IgE may be helpful in such cases.

Cells of the Immune System

White blood cells (WBCs) or leukocytes are cells of the immune system that defend the human body against infectious disease and foreign materials and are often characterized as granulocytes or agranulocytes, depending on the presence or absence of granules. There are various types of leukocytes, which are all produced in the bone marrow and derived from (multipotent) hematopoietic stem cells. Leukocytes are found throughout the body, including the blood and lymphatic system.

Granulocytes feature differently staining granules in their cytoplasm when viewed under light microscopy. These granules are membrane-bound enzymes that primarily act in the digestion of endocytosed particles. There are three types of granulocytes that are named according to their staining properties: (a) neutrophils, (b) basophils, and (c) eosinophils.

Agranulocytes lack granules in their cytoplasm, but they do contain lysosomes and include lymphocytes, monocytes and macrophages.

Granulocytes

Basophils

Basophil granulocytes or basophils form part of the polymorphonuclear cell family (PMNs) together with eosinophils and neutrophils. They contain prominent cytoplasmic granules that readily stain with dyes and are therefore called basophilic (susceptible to staining by dyes) granulocytes or basophils. They are the least common of the granulocytes, representing less than 1% of the circulating white blood cells. Based on their similar morphology to mast cells, basophils have often been considered as minor and possibly redundant "circulating mast cells". The isolation of pure basophils has been a challenge due to the low occurrence in blood and due to the fact that basophils share many physiochemical properties with other blood cells, all which considerably hampered basophil research and negatively affected interest in this type of cells.

Apart from the cytoplasmic granules, basophils constitutively express high affinity IgE receptors (FcεRI) and are a major source of the vasodilator histamine and other potent chemical mediators of inflammation. Like all leukocytes, basophils develop in the bone marrow, derive from hematopoietic stem cells and are released as fully mature cells with a life span of 2-3 days.

Basophils express a variety of seven membrane transverse receptors that bind chemotactic factors. Most are members of the CCR family of receptors that bind CC (cysteine-cysteine-bonded) chemokines. There are at least 27 distinct members of this subgroup reported for mammals, called CC chemokine ligands (CCL)-1 to -28. CC chemokines induce the migration of monocytes and other cell types such as natural killer (NK) and dendritic cells. Examples of CC chemokine include monocyte chemoattractant protein-1 (MCP-1 or CCL2) which induces monocytes to leave the bloodstream and enter the surrounding tissue to become tissue macrophages.

Human basophils also express a variety of cytokine receptors for interleukins, chemokines, complement, prostaglandins, and immunoglobulin FC receptors, all which help transmit the signal of cytokines in the immune system. Among these are receptors that bind to specific interleukins including interleukin-2 (IL-2), IL-3, IL-4, IL-5, and IL-33. Basophils are one of the few cells that express the IL-3 receptor, which is also known as CD123 antigen or CD 123.

This characteristic has led to use CD123 expression, in addition to other CD (cluster of differentiation) markers, as a marker to specifically gate on basophils during flow cytometry analysis.

The high affinity IgE receptor (FcεRI) is thought to be the single most significant activation-linked molecule known on basophils. These receptors are comprised of four subunits: one α, one β, and two γ chains that form a tetramer structure (αβγ2). Two extracellular domains on the α-subunit allow IgE binding, whereas signaling events are initiated through immunoreceptor tyrosine-based activation motifs located within intracellular portions of the β-subunits and γ subunits. In humans, a trimeric (αγ2) form of FcεRI is also found on antigen-presenting cells, including Langerhans cells, monocytes and blood dendritic cells. Mast cells, eosinophils, neutrophils, platelets and dendritic cells may have these and/or functionally related receptors, too.

Basophils can infiltrate sites of many immunologic or inflammatory processes, including IgE-associated late-phase reactions and sites of chronic allergic inflammation, often in association with eosinophils. Further, basophils can be involved in IgE independent mechanisms. Generally, basophils can be activated by a number of stimuli and give rise to distinct activation pathways. Those stimuli might or might not be mediated by the high-affinity IgE receptor (FcεRI).

Basophils release several inflammatory mediators that have a role in the pathophysiology of allergic disease. The most commonly recognized inflammatory mediators are histamine and leukotriene C4 (LTC4), which cause smooth muscle contraction. It long has been thought that basophils release these substances during and/or after selectively infiltrating sites of allergic inflammation and thus contribute towards the symptoms of the late phase response. Basophils circulate in the blood under homeostatic conditions, but will migrate into tissue during the late phase response, which, upon reexposure to an offending allergen, follows the acute allergic reaction.

In humans, basophils appear to be the prime early producers of the Th2-type cytokines IL-4 and IL-13, which perform several crucial functions in initiating and maintaining allergic responses. The assumed immunomodulatory role of basophils is further supported by their ability to express CD40 ligand, which, together with IL-4 and IL-13, serve as inducers of B cell proliferation and class switching to IgE and IgG.

The cluster of differentiation (CD) system is a protocol used for the identification of cell surface molecules present on white blood cells. CD markers can act in numerous ways, often acting as receptors or ligands, by which a signal cascade is initiated, altering the behavior of a cell. Generally, a proposed surface molecule is assigned a CD number once two specific monoclonal antibodies (mAb) are shown to bind to the molecule. If the molecule has not been well-characterized, or has only one mAb, the molecule is usually given the provisional indicator "w". The CD system nomenclature commonly used to identify cell markers thus allows cells to be defined based on what molecules are present on their surface. There are more than 350 CD molecules identified for humans, and several CD molecules are usually utilized to define a population of cells, in particular through cell sorting methods that include flow cytometry. Cell populations are usually defined using a "+" or "−" symbol to indicate whether a certain cell fraction expresses or lacks a certain CD molecule. For example, all hematopoietic cells express CD45, and thus are defined as CD45+. Furthermore, all granulocyte cells express in addition CD15, so they are defined as CD45+, CD15+. Stem cells are commonly characterized by several CD markers, including by the expression of CD34 and the lack of CD31, as defined as CD34+, CD31−.

Most CD molecules have important functions beyond their use as cell surface markers; for example CD 123 that is expressed by basophils, as mentioned supra, induces tyrosine phosphorylation with the cell and promotes proliferation and differentiation within the hematopoietic cell lines. CD203c is another CD marker that is expressed on the cell surface and within intracellular compartments of basophils, mast cells and precursors of these cells. CD203c detection by flow cytometry has been used to specifically identify basophils within a mixed leukocyte suspension, since its expression is unique to basophils among the cells circulating in blood. The expression of CD203c is both rapidly and markedly upregulated following IgE-dependent activation. CD63, a cell surface glycoprotein of the transmembrane 4 superfamily, is also upregulated following IgE-dependent cell activation, however, like CD203c, is not specific enough to serve reliably as a diagnostic marker for the diagnosis of IgE-mediated allergic reactions. Apart from their marker function, CD molecules have other tasks that include the facilitation of cell attachment, phagocytosis and chemotaxis as well as the recruitment of kinases.

Eosinophils

Eosinophil granulocytes or eosinophils are primarily tissue-dwelling granulocytes that are recruited to sites of acute inflammation, and are seen most prominently in response to respiratory, gastrointestinal, and dermatologic allergens, as well as to generalized infection with helminthic parasites. Eosinophils have been found to have innate capacities to secrete differentially multiple preformed cytokines. Eosinophil-associated allergic inflammatory diseases notably occur in the airways and include asthma and rhinorrhea. Eosinophils that are recruited into the mucosal airway tissues and secretions are positioned to encounter aeroallergens where they may function as antigen-presenting cells. For example, in humans, blood eosinophils, which normally do not display Major Histocompatibility Complex (MHC) class II proteins, can be induced to do so by stimulation with cytokines, including GM-CSF, IL-3, Il-4, Il-5 and interferon-γ (IFN-γ). On most immune system cells, specifically on antigen-presenting cells, MHC class II proteins contain α and β chains and present antigen fragments to T-helper cells by binding to the CD4 receptor on the T-helper cells. Moreover, human eosinophils recruited into the airways, as evidenced in the sputum of asthmatics and in lung lavages after allergen challenges, typically express MHC II proteins. Unlike the gastrointestinal tract, where eosinophils normally are found and might be exposed to gut-derived antigens, eosinophils are not abundant in the normal lungs or airways. In contrast, recruitment of eosinophils into the upper and lower airways is a frequent concomitant of allergic inflammation. It is in this setting of allergic airways diseases that recruited eosinophils might function not simply as effectors of local inflammation, but also as "inflammatory" full-function antigen-presenting cells in processing and presenting airway antigens. In the context of allergic upper and lower airways diseases in which eosinophils are characteristically elicited, the capacity of eosinophils to serve as additionally recruited "inflammatory" full-function antigen-presenting cells could be pertinent to antigen-elicited immune responses in the airways of those with often chronic, eosinophilic allergic diseases.

Neutrophils

Neutrophil granulocytes or neutrophils are the most abundant type of white blood cells in mammals by representing between 40% and 50% of the circulating leukocyte population and form an essential part of the innate immune system. The name, neutrophil, derives from particular staining characteristics on histological and/or cytological preparations. Whereas basophils stain dark blue and eosinophils stain bright red, neutrophils stain a neutral pink. Neutrophils are normally found in the blood stream. However, during the acute phase of inflammation, neutrophils are one of first-responders of inflammatory cells to migrate toward the site of inflammation, first through the blood vessels, then through interstitial tissue, following chemical signals such as IL-8 and IFN-gamma in a process called chemotaxis. Neutrophils are recruited to the site of injury within minutes following trauma and are the hallmark of acute inflammation.

Neutrophils are crucial to both immunity and inflammation, and prolonged neutropenia (a decrease in the number of neutrophils) leads inevitably to life-threatening situations as a result of insufficient protection against infections. Circulating neutrophils are quiescent cells with only the potential to mediate a wide range of inflammatory activities; this potential is realized when neutrophils are activated by agents including, but not limited to, leukotriene B4 (LTB4), complement fragment C5a, platelet activating factor (PAF), histamine, IFN-γ, granulocyte colony-stimulating factor (G-CSF), granulocyte-macrophage colony-stimulating factor (GM-CSF), IL-8, tumor necrosis factor-α (TNF-α) and different chemoattractants. Those activating agents transmit signals to neutrophils via interaction with specific cell surface receptors, many of which interact with intracellular G proteins. G proteins catalyze the hydrolysis of guanosine triphosphate (GTP) to guanosine diphosphate (GDP) and inorganic phosphate, and initiate a series of events including activation of phospholipase C, initiation of calcium fluxes and membrane depolarization. Once activated, neutrophils are able to adhere to endothelial cells, migrate through the endothelial barrier, and ingest and attempt to destroy pathogens, foreign bodies, and remnants of tissue damage. Activated neutrophils exhibit an enhanced response to subsequent stimuli.

Agranulocytes

Agranulocytes are characterized by the absence of stainable granules in their cytoplasm, but they do lysosomes. Agranulocytes include lymphocytes, monocytes and macrophages.

Study of Intracellular Mechanism in Basophils, Eosinophils and/or Neutrophils to Observe Cell Activation The mechanisms that govern basophil activation and the activation of other granulocytes are complex and incompletely understood. What is understood is that the different pathways that give rise to granulocyte activation and mediator (e.g. histamine) release are accompanied by consecutive protein phosphorylation cascades. Therefore, the intracellular analysis of transcriptional activation might aid in detecting early changes in granulocytes.

The simultaneous intracellular detection of phosphorylated and non-phosphorylated signaling molecules (phosphoepitopes) in granulocytes was of particular interest in the present invention in order to study signal transduction in basophils, eosinophils and/or other granulocytes at a single cell level. Granulocytes, in particular basophils and eosinophils, can be activated by a number of stimuli and give rise to distinct intracellular signaling pathways, which involve phosphorylation of some target protein and which lead to the main effector functions, including, but not limited to, mediator (e.g. histamine) release, leukotriene generation and cytokine production.

Intracellular Signaling Molecules

Targets of intracellular phosphorylation include, but are not limited to, intracellular transcription factors, kinases and phosphoproteins.

Signal Transducers and Activator of Transcription (STAT) Proteins (aka Signal Transduction and Transcription Proteins)

The STAT proteins regulate many aspects of cell growth, survival and differentiation. The transcription factors of this family are activated by the Janus Kinase JAK and dysregulation of this pathway is frequently observed in primary tumors and leads to increased angiogenesis, enhanced survival of tumors and immunosuppression. Knockout studies have provided evidence that STAT proteins are involved in the development and function of the immune system and play a role in maintaining immune tolerance and tumor surveillance.

There are seven STAT proteins, namely STAT1, STAT2, STAT3, STAT4, STAT5A, STAT5B and STAT6. STAT proteins were originally described as latent cytoplasmic transcription factors that require phosphorylation for nuclear retention. The unphosphorylated STAT protein shuttles between cytosol and the nucleus waiting for its activation signal. Once the activated transcription factors reaches the nucleus it binds to a consensus DNA-recognition motif called gamma activated sites (GAS) in the promoter region of cytokine inducible genes and activates transcription of these genes.

Phospho-STAT1 is involved in IL-5 signaling in eosinophils. IL-5 is a critical cytokine for eosinophil growth and function, and mouse models of Eosinophilic Esophagitis (EoE) have demonstrated the importance of IL-5 for eosinophil trafficking to the esophagus. Phospho-STAT 6 mediates IL-4 signaling, which plays a role in immunoglobulin (Ig) E production, and patients with EoE tend to have high rates of IgE-mediated food and aeroallergen hypersensitivity. Furthermore, in certain cell types, STAT6 also mediates the expression of eotaxin, a major chemoattractant for eosinophils in EoE.

Flow Cytometry

The availability of monoclonal antibodies directed against phosphorylated epitopes (phosphoepitopes) and the availability of intracellular staining procedures made flow cytometry an ideal approach for studying signaling pathways in granulocytes.

Flow cytometry is a technique for counting and examining small particles such as cells by suspending them in a stream of fluid and passing them by an electronic detection apparatus. It allows simultaneous multiparametric analysis of the physical and/or chemical characteristics of each individual particle or cell. Briefly, a beam of light (usually laser light) of a single wavelength is directed onto a hydrodynamically-focused stream of fluid. A number of detectors are aimed at the point where the stream passes through the light beam: one in line with the light beam (forward scatter), several in perpendicular position (side scatter) and at least one fluorescence detector. Each suspended cell (from 0.15 μm-150 μm) passing through the light beam scatters the light in some way, and fluorescent molecules (naturally occurring or as part of an attached label or dye) may be excited into emitting light at a longer wavelength than the light source. This combination of scattered and fluorescent light is recorded by detectors. The forward scatter correlates with the cell volume, while the side scatter depends upon the inner complexity of the cell (such as shape of the nucleus). The data generated by flow-cytometers can be plotted in a single dimension to produce a histogram or in two-dimensional or three dimensions plots. The regions on these plots can be sequentially separated, based on fluorescenc intensity, by creating a series of subset extractions, termed "gates." Specific gating protocols exist for diagnostic and clinical purposes, especially for hematology. There are also flow cytometers who only use light scatter, without fluorescence, for the analysis.

Fluorescence activated cell sorting (FACS) is a specialized type of flow cytometry and provides a method of sorting a heterogeneous mixture of cells into two or more containers, a single cell at a time, based upon the specific light scattering and fluorescent characteristics of each cell. The use of multicolor, multiparameter FACS requires primary conjugated antibodies at defined fluorophore-to-protein (FTP) ratios.

The cell suspension is entrained in the center of a narrow, rapidly flowing stream of liquid and the flow is arranged so that there is a large separation between cells relative to their diameter. The stream of individual cells passes through a fluorescence detector, and an electrical charge is assigned to each cell (based on the cell's fluorescence) just at the point where the stream breaks into individual droplets (usually via a vibrating mechanism) such that there is a low probability that more than one cell per droplet occurs. Each charged droplet (containing an individual cell) may be sorted, via electrostatic deflection, into separate containers.

The surfaces of all cells in the body are coated with specialized protein receptors that selectively can bind or adhere to other signaling molecules. These receptors and the molecules that bind to them are used for communicating with other cells and for carrying out proper cell functions in the body. Each cell type has a certain combination of receptors or cell markers on its surface that makes it distinguishable from other kinds of cells. Cells may, for example, be fluorescently or radioactively labeled. The most commonly used labeled molecules are antibodies; their specificity towards certain surface markers on a cell surface allows for more precise detection and monitoring of particular cells. The fluorescence label that can be used will depend upon the lamp or laser used to excite the fluorochromes and on the detectors available.

The development of flow-cytometry based approaches for the identification of activation markers and intracellular markers, via measurement of enzymatic and surface marker profiles, has allowed for accelerated association of surface topologies with disease states. Studies that involve the triggering of cells to respond to environmental stimuli, such as an allergen or drug action, and the activation phenotypes associated with such agitation, allow for clearer resolution of the underlying activation states and provide for more distinct classification of allergic disease outcomes. Allergy is a dynamic event, and as such, static views of basal states would be considered insufficient for determination of an activated state, therefore rendering correlations to clinical outcomes less meaningful. Fractionation of cell populations with flow cytometry is well suited to address activation markers and intracellular markers in the context of allergic disease, because it can simultaneously discern multiple surface markers within complex cellular populations.

Utility

Important Role of Granulocytes in Allergic Response

The analysis of subpopulations of white blood cells (leukocytes) in blood or bone marrow is of particular interest for the evaluation of immune system disorders and immune system-related diseases, especially allergic diseases. Basophils, neutrophils and eosinophils play important roles in the allergic response to an offending allergen and/or environmental stimulus. Upon activation by an allergen and/or stimulus, basophils, eosinophils and/or neutrophils can exhibit changes on their cell surfaces and/or inside the cell which can be detected, classified and correlated with the particular allergen or stimulus with the objective to identify an offending allergen or stimulus to which a mammalian subject is allergic.

Blood-Based Allergen Testing

Carrying out testing for offending allergens in blood cells offers the great advantage that a blood sample can quickly and without much discomfort be obtained from a mammalian subject. Furthermore, the testing for an offending allergen is done by ex vivo activation, which means that the offending allergen is not directly ingested (or otherwise administered) by the mammalian subject, but the offending allergen is added to an isolated fraction of a blood sample drawn from the particular mammalian subject. This way, the subject is in no way endangered to experience a potentially life-threatening allergic reaction, as it would be if the subject had to ingest an offending allergen, as is the case in in-vivo food challenge tests, or if the subject had to be externally administered an offending allergen, as is the case in conventional allergy skin tests.

An in-vivo food challenge test is generally carried out in a double-blind, placebo-controlled fashion to determine the offending allergen. This test is not only difficult to administer, but it is also very time-consuming and, most importantly, potentially highly dangerous since it can result in anaphylactic shock and even death, if treatment is not initiated quickly.

Conventional allergy skin tests, where several potentially offending allergens are subcutaneously administered together with histamine as positive control to a subject, are less dangerous in that they usually don't evoke a life-threatening anaphylactic shock situation. However, the subcutaneous administration is usually discomforting, in particular for a pediatric subject, and often inconclusive, since the extent of a potentially positive indication on the skin ('skin reaction'), as determined when the spot where a potential allergen or stimulus was administered start to inflame or appears inflamed within a certain time (usually 15-60 minutes), does not necessarily correlate with a true allergic response. Hence, a weak skin reaction can still be followed by a strong allergic response, whenever the subject is exposed to the offending allergen in a real life situation. Vice versa, a strong skin reaction that indicates a strong allergy to the offending allergen, can nevertheless be followed by only a slight, subtle, possibly not even noticeable allergic response, whenever the subject is exposed to the offending allergen or stimulus in a real life situation.

Rapid, Safe and Reliable Blood-Based Susceptibility Testing to Offending Allergens Other approaches that attempt to monitor or determine the activation status of granulocytes are often based on simply counting white blood cells upon granule-staining by manual or automatic means or separating white blood cells by density gradient and subsequent cell sorting. While these methods are time-consuming and can only provide an estimate, they are seriously deficient in their reliability because those methods don't distinguish well live from dead cells and don't provide any insights into what is going on inside the cells, in particular, inside of granulocytes.

The described invention, in contrast, provides the ability to monitor cell activation in biological samples such as whole blood, in particular in white blood cells such as live basophils and live eosinophils that are specifically gated and labeled for the determination of their activation status. The described invention, furthermore, allows for a safe and time-efficient evaluation without endangering the subject who is undergoing the testing, by measuring said activation status ex vivo and in a straight-forward manner from blood sampling to cell separation, ex-vivo activation and determination of activation status. By specifically evaluating internal cell markers such as internal phosphoepitopes in activated granulocytes in comparison to non-activated granulocytes from the same whole blood sample that was provided by the the subject who is undergoing the testing, the monitoring and evaluation of response of the subject to an offending allergen or stimulus is reliable and sensitive.

Monitoring of Allergy Treatment Success

Consistent allergen avoidance would be ideal and would obviate the need for allergy treatment, but is not practical or feasible. The quality of life of a subject that is susceptible to one or more offending allergens is greatly affected by the quality of allergy treatment management that he/she receives. It is important to monitor a subject receiving allergy treatment to determine whether and, if yes, how well the disease is kept under control, whether the subject is compliant with therapy and how well the subject responds to the chosen therapy so that the allergy/allergic disease does not exacerbate and escalates in a major, life-threatening allergic reaction/anaphylaxis. Successful therapeutic monitoring will at last not only improve the subject's quality of life, it will also reduce the subject's state, duration and frequency of morbidity and need for urgent medical intervention. Certain embodiments of the present invention describe the ex-vivo detection of intracellular signaling, e.g. phosphoepitopes, in live basophils, eosinophils and/or neutrophils of a subject, that is under ongoing allergy treatment, at baseline level, i.e. without any external stimulation of an offending allergen in order to determine and monitor that subject's responsiveness to the allergy treatment. The monitoring requires repeated testing at specified time interval (daily, weekly, biweekly, monthly and so forth) and comparison of the test results to enable a reliable determination of therapy progress and success Diseases and disorders where this method will be useful are food allergy, airborne allergy, drug-induced allergy (suspected, based on medical history, or more importantly, in absence of a known predisposition), anaphylaxis, asthma and other immune disorders.

Particular embodiments of the present invention use very small volumes of whole blood (100 µl or less per assay) and so are also suitable for studies in infants, children, healthy and sick individuals. The blood samples are generally obtained by venipuncture and are immediately put on ice and further processed at 4° C. to preserve optimal cellular viability and functionality.

Mammalian Subjects/Pediatric Mammalian Subjects/Sick Mammalian Subjects

The above-described methods may be performed on a mammalian subject, e.g., a human being or some other member of a species of mammalian origin, who is: a) suspected of having an allergy to some offending allergen or stimulus, based on medical history or known predisposition or b) is not suspected of having an allergy to some offending allergen or stimulus, in the absence of a known predisposition, to determine if that subject has an allergy to some offending allergen or stimulus.

Since the methods of the present invention to evaluate a subject for any kind of allergic response to an offending allergen or stimulus only require one drop (100 µl or less) of blood per analysis, they are ideally suited for testing all type of subjects (e.g. children, small children, infants as well as sick subjects who cannot afford to provide much blood for analysis).

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples and experimental procedures will be described to illustrate parts of the invention.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Functional Isolation of Granulocytes for Analysis

To functionally isolate granulocytes for analysis, the present invention uses a flow cytometric method in which the unstimulated and the stimulated blood sample are stained with a specialized combination of fluorochrome-coupled monoclonal antibodies and other staining reagents. The combination is designed to enable detection of the relevant intracellular and surface markers in granulocytes while excluding dead cells and all other viable blood cells from the analysis. Thus, we use reagents that reveal cell viability, specifically detect basophils or other granulocytes surface markers and reveal intracellular phosphoepitopes and/or other epitopes that are modified in response to specific stimulation. Importantly, the invention is based on the use of staining reagents whose reactivity with relevant determinants remains detectable after cell permeabilization by methanol, as described in patent applications U.S. Ser. No. 61/110,283 and U.S. Ser. No. 12/610,940, which entirely are incorporated by reference.

Example 2

Exemplary Experimental Procedure

In embodiments of the present invention, we identify allergens to which a patient may be immune by adding the patient's own plasma to his own whole blood samples and the suspected allergens (suspected, based on medical history, or more importantly, in absence of a known predisposition). When IgE or other immunoglobulins (Ig) capable of binding the immunogen and triggering granulocyte stimulation are present in the sample, surface marker changes, up-regulation or down-regulation of protein phosphorylation and other internal biochemical shifts occur in the granulocytes. Staining for these stimulation-induced changes with an assay that allows their specific detection in basophils and/or other granulocytes reveals allergy-dependent Ig in patient plasma and thus allows specific detection of offending antigens in individual patients.

Protocol. We stimulated each blood sample from the patient (less than 100 μL) by adding his own plasma depleted in platelets (50/50 v/v) and the suspected allergen (food, environmental, microbial, nanoparticle, metal and drug related extract allergens) for 10 to 30 minutes at controlled temperature. Then, we stained for the activation surface markers and for the intracellular phosphoepitopes, as described in patent applications U.S. Ser. No. 61/110,283 and U.S. Ser. No. 12/610,940, which entirely are incorporated by reference.

Example 3

Detection of Basophils, Neutrophils and Eosinophils from Whole Blood (Without Any Stimulation)

As shown in FIG. 1, basophils, neutrophils as well as eosinophils can simultaneously be analyzed from one drop of blood without requiring any purification or separation step.

Example 4

Intracellular Signalisation Detection in Live Basophils, Eosinophils and Neutrophils from Whole Blood (Without Any Stimulation)

As shown in FIG. 2, intracellular signaling in basophils, neutrophils as well as eosinophils can simultaneously be detected from one drop of blood without requiring any purification or separation step.

Example 5

Phosphorylated STAT1 and STAT6 in Blood Leukocytes as Disease Indicators in Eosinophilic Esophagitis Whole blood-based measurements of phosphorylated-signal transducer and activator of transcription (phospho-STAT) 1 and 6 levels in eosinophils, neutrophils, and CD3+ lymphocytes proved useful in identifying eosinophilic esophagitis (EoE) patients and in monitoring therapeutic outcomes.

Subsets of leukocytes (basophils, eosinophils, neutrophils, lymphocytes) were identified directly from 50 μl of whole blood from patients suffering from EoE and from healthy control subjects using whole blood staining methodology, as described supra. Using digital flow cytometry, levels of chosen intracellular phosphoepitopes, including phospho-STAT 1 and phospho-STAT6, were measured within each cell subset.

Levels of phospho-STAT1 and phospho-STAT6 in blood eosinophils, neutrophils and CD3+ lymphocytes were found to be significantly higher for untreated EoE patients compared to healthy control subjects ($P \leq 0.010$).

Median fluorescence intensities of the phosphoepitopes of interest were measured for live neutrophil and eosinophil subsets (gated as Live/Dead-negative, CD3-negative, and CD16-positive, CD66b-positive (neutrophils), or CD16-negative, CD66b-positive (eosinophils)) and live CD3+ lymphocyte subset (gated as Live/Dead-negative and CD3-positive) (see FIG. 3).

Phospho-STAT1. A summary of cell-based phospho-STAT measurements is presented in Table III. In blood eosinophils (see FIG. 4A), neutrophils (see FIG. 4B) and lymphocytes (see FIG. 4C) intracellular levels of phospho-STAT1 were significantly higher for untreated EoE subjects compared with HC subjects ($P \leq 0.0078$, $P \leq 0.0026$, and $P \leq 0.0106$, respectively; N=7 untreated EoE subjects and 8 HC subjects).

TABLE III

Summary of Cell-based Phospho-STAT Measurements

| Sub. # | Eosinophil Phospho-STAT1 | Eosinophil Phospho-STAT6 | Neutrophil Phospho-STAT1 | Neutrophil Phospho-STAT6 | CD3+ Lymphocyte Phospho-STAT1 | CD3+ Lymphocyte Phospho-STAT6 |
|---|---|---|---|---|---|---|
| 1 | 149 | 236 | 83 | 62 | 44.8 | 34.9 |
| 2 | 79 | 189 | 33.7 | 31.7 | 8.8 | 5.9 |
| 3 | 360 | 632 | 113 | 103 | 22.6 | 19.7 |
| 4 | 378 | 292 | 116 | 62 | 43.5 | 62.2 |
| 5 | — | 129 | — | 29 | — | 22.7 |
| 6 | 491 | 857 | 118 | 73 | 7.6 | 17.1 |
| 7 | 121 | 247 | 53.4 | 44.4 | 32.1 | 23.9 |
| 8 | 175 | 2376 | 27 | 350 | 23.5 | 216.9 |
| 1* | 13 | 20 | 16.7 | 22.7 | 15 | 18.6 |
| 9 | 88 | 93 | 4.7 | 7.5 | 5.9 | 6.7 |
| 10 | — | 221 | — | 17.6 | — | 14 |
| 11 | 78 | 156 | 91.3 | 99.3 | 8.1 | 8.2 |
| 12 | 81 | 109 | 67.4 | 64.4 | 34.5 | 18.7 |

*Subject #1 was included in the study at two time points, before and 5 weeks after starting an elemental diet. Phospho-, phosphorylated; STAT, signal transducer and activator of transcription; —, Data not available. All units are median fluorescence intensities (MFI).

Phospho-STAT6. In blood eosinophils (see FIG. 4D), neutrophils (see FIG. 4E) and CD3+ lymphocytes (see FIG. 4F), intracellular phospho-STAT6 levels were significantly higher for untreated EoE subjects compared with HC subjects ($P \leq 0.0055$, $P \leq 0.0026$, and $P \leq 0.0321$, respectively; N=8 untreated EoE subjects and 7 HC subjects).

Furthermore, levels of phospho-STAT1 and phospho-STAT6 in blood eosinophils were significantly higher for untreated EoE patients compared with treated EoE subjects who had received their prescribed therapy ($P \leq 0.0233$ (phospho-STAT1) and $P \leq 0.0128$ (phospho-STAT6)).

Phospho-STAT1. In blood eosinophils, phospho-STAT1 levels were significantly lower for EoE subjects with prescribed therapy compared with untreated subjects (see FIG. 4A; $P \leq 0.0128$; N=7 untreated EoE subjects and 4 EoE subjects with therapy). In particular, subject #1 showed an approximate 11-fold decrease in phospho-STAT1 levels in blood eosinophils after 5 weeks on an elemental diet (MFI of 149 before therapy vs. MFI of 13 after 5 weeks of therapy).

Phospho-STAT6. In blood eosinophils, phospho-STAT6 levels were significantly lower for EoE subjects with therapy compared with untreated subjects (see FIG. 4B; P≤0.0128; N=8 untreated EoE subjects and 5 EoE subjects with therapy). In particular, subject #1 showed an approximate 11-fold decrease in phospho-STAT6 levels in blood eosinophils after 5 weeks on an elemental diet (MFI of 236 before therapy vs. MFI of 20 after 5 weeks of therapy).

Additional phosphoepitopes. Intracellular levels of phospho-STAT4 were also measured in blood eosinophils, neutrophils, and CD3+ lymphocytes of EoE and control subjects, but no significant differences were observed (see FIGS. 4G-I). Other phosphoepitopes tested which also showed no significant differences included phospho-Akt, phospho-SRC, phospho-Syk, and phospho-S6 ribosomal protein (see FIGS. 6-9).

Phospho-STAT6 Levels in Blood Neutrophils Correlate with Eosinophil Counts in Esophageal Tissues of EoE Subjects We tested whether cell-based measurements of phospho-STAT1 and phospho-STAT6 levels in blood eosinophils, neutrophils, and CD3+ lymphocytes in all EoE subjects correlate with each other and with the number of eosinophils per high-power field in esophageal tissues, a key disease parameter of EoE (see Table IV). Interestingly, in eosinophils, intracellular phospho-STAT1 levels correlated positively with phospho-STAT6 levels (R=0.85; P≤0.0010). Similarly, in CD3+ lymphocytes, phospho-STAT1 levels correlated positively with phospho-STAT6 levels (R=0.80; P≤0.0031). Phospho-STAT1 levels in eosinophils also correlated positively with phospho-STAT1 levels in neutrophils (R=0.62; P≤0.0426). Furthermore, phospho-STAT6 levels in eosinophils correlated positively with phospho-STAT6 levels in neutrophils (R=0.66; P≤0.0140). Importantly, phospho-STAT6 levels in neutrophils also correlated positively with the number of eosinophils per high-power field in distal (R=0.73; P≤0.0384) and proximal (R=0.74; P≤0.0360) esophageal tissues of EoE subjects.

TABLE IV

Statistically Significant Pairwise Correlations

| Parameter 1 | Parameter 2 | R (Spearman test) | P value (Spearman test) |
|---|---|---|---|
| CD3+ lymphocyte phospho-STAT1 | CD3+ lymphocyte phospho-STAT6 | +0.80 | 0.0031 |
| Eosinophil phospho-STAT1 | Eosinophil phospho-STAT6 | +0.85 | 0.0010 |
| Eosinophil phospho-STAT1 | Neutrophil phospho-STAT1 | +0.62 | 0.0426 |
| Eosinophil phospho-STAT6 | Neutrophil phospho-STAT6 | +0.66 | 0.0140 |
| Neutrophil phospho-STAT6 | Eos/hpf in distal esophagus | +0.73 | 0.0384 |
| Neutrophil phospho-STAT6 | Eos/hpf in proximal esophagus | +0.74 | 0.0360 |

Eos/hpf, Number of eosinophils per high-power field (at 400X magnification) in esophageal tissues. N = 12 EoE subjects included.

Plasma Markers do not Appear to be Predictive of Therapeutic Effect

We tested whether plasma markers could be used in conjunction with phospho-STAT1 and phospho-STAT6 as disease indicators for EoE. The plasma molecules we studied were each known to be associated with STAT1 and/or STAT6 signaling, or with the development of EoE. A summary of fluid assay measurements is presented in Table E1 of the Online Repository. Among the plasma molecules studied, levels of IgE were significantly higher in plasma of untreated EoE subjects compared with HC subjects (see FIG. 3A). Similarly, levels of IgE were also significantly higher in plasma of EoE subjects with therapy compared with HC subjects (see FIG. 3A). Though there was a trend of higher levels of IL-4, eotaxin-1, and interferon-gamma (IFN-γ) in plasma of untreated EoE subjects compared with HC subjects, these plasma molecules did not distinguish between EoE subjects with and without therapy (see FIGS. 3B-D). No significant differences in plasma IL-5 or IL-15 levels were observed between the subject groups studied (see FIGS. 3E-F). Furthermore, levels of these plasma markers were not correlated with intracellular phospho-STAT levels.

Subjects

The study was approved by the Stanford Administrative Panel on Human Subjects in Medical Research. All subjects (or subjects' parents/guardians for minors) gave written, informed consent and underwent thorough allergy testing and completed a comprehensive questionnaire regarding medical history and allergy status before participating. Whole blood staining analysis (see below) was performed using the same method for all subjects prior to the assessment of their diagnosis and treatment status based on medical history. EoE subjects were distinguished from subjects with gastroesophageal reflux disease and other gastric diseases based on the subjects' unresponsiveness to acid suppression therapy and on the presence of 15 or more eosinophils per high-power field in esophageal biopsies. Subjects with EoE were divided into two groups: untreated and with prescribed therapy. Therapy for EoE included swallowed steroids or anti-interleukin (IL)-5 therapy (mepolizumab) or elemental diet. EoE subjects in the untreated group included those who were not on any medications for EoE at the time of sampling. Subjects were under 20 years of age, and healthy control (HC) subjects were age- and gender-matched volunteers. Healthy controls had no gastrointestinal symptoms, no acute disease, and no chronic disease at the time of sampling.

Clinical Characteristics of Subjects

The clinical features of the EoE subjects enrolled in this study are summarized in Tables I and II. Twelve subjects diagnosed with EoE were included (9 males and 3 females; age range, 3-19 years). The most commonly reported symptoms among EoE subjects included abdominal pain and dysphagia. None of the subjects had hypereosinophilia.[23] The following subjects had been prescribed the following therapies for EoE at the time of study: subjects #9 and #11 with swallowed budesonide, subject #10 with anti-IL-5 therapy, and subject #12 with swallowed fluticasone. Also, subject #1 was included in the study at two time points, before and 5 weeks after starting an elemental diet.

TABLE I

Clinical Characteristics of Study Subjects (part 1/2)

| Group | Sub. # | Sex/Age (y) | Gastroenterological Symptoms | Prescribed Therapy for EoE |
|---|---|---|---|---|
| EoE Untreated | 1* | F/3 | Moderate epigastric pain | None |
|  | 2 | M/4 | Abdominal pain | None |
|  | 3 | F/6 | Vomiting, abdominal pain | None |
|  | 4 | M/8 | Severe dysphagia, food impaction | None |
|  | 5 | F/9 | Vomiting | None |
|  | 6 | M/11 | Food impaction | None |
|  | 7 | M/13 | None | None |
|  | 8 | M/15 | Moderate dysphagia | None |
| EoE with Therapy | 1* | F/3 | Mild abdominal pain | Elemental diet |
|  | 9 | M/9 | None | Swallowed budesonide |
|  | 10 | M/11 | Coughing | Anti-IL-5 therapy |
|  | 11 | M/18 | Dysphagia, food impaction | Swallowed budesonide |
|  | 12 | M/19 | None | Swallowed fluticasone |

Sub. #, Subject number;
EoE, Eosinophilic esophagitis;
M, Male;
F, Female.

TABLE II

Clinical Characteristics of Study Subjects (part 2/2)

| Sub. # | Gross Appearance of Esophagus | # Eos/hpf in Esophagus | % Eos in blood | Food Allergies | Other Allergic Disorders |
|---|---|---|---|---|---|
| 1 | Furrowing | D > 16, P > 20 | 10.5 | Eggs, milk, nuts | Allergic rhinitis |
| 2 | Furrowing, white plaques | D > 25, P > 25 | 17.1 | None | Allergic rhinitis |
| 3 | Furrowing, narrowing | D > 35, P > 50 | 30.9 | Eggs, nuts | Asthma |
| 4 | Mild furrowing, white plaques | D = 12, P = 20 | 23.6 | Eggs, legumes milk Nuts, soy | Asthma |
| 5 | — | — | 7.5 | Nuts | Allergic rhinitis |
| 6 | Slightly fryable | D = 25, P = 25 | 20.8 | Milk, nuts, potatoes, wheat | Allergic conjunctivitis, allergic rhinitis |
| 7 | Normal | D = 16, P = 0 | 2.75 | Beef, milk | None |
| 8 | Furrowing, trachealization | D = 30, P = 30 | 11.3 | Tomatoes | None |
| 1* | Normal | D < 5, P < 5 | 1 | Eggs, milk, nuts | Allergic rhinitis |
| 9 | — | — | 19.1 | Eggs, milk, pork, soy | Allergic rhinitis |
| 10 | — | None | 2.08 | Eggs, nuts | Environmental allergies |
| 11 | — | — | 15.5 | None | Environmental allergies |
| 12 | Furrowing, abscesses, trachealization | — | 18.2 | Eggs, milk | Allergic rhinitis |

D, Distal esophagus; P, Proximal esophagus; #Eos/hpf in esophagus, Number of eosinophils per high-power field (at 400X magnification) in esophageal tissues; % Eos in blood, Percentage of eosinophils in blood; —, Data not available.

Collection and Processing of Samples

Four milliliters of blood in a BD Vacutainer tube (containing 7.2 mg EDTA) were obtained during diagnostic and follow-up blood draws. To limit artifactual activation of blood leukocytes as much as possible, samples were placed on ice immediately upon collection, and all subsequent staining steps were done at 4° C. Briefly, blood was first centrifuged (10 minutes, 400 G) to remove the plasma and resuspended to its original volume with phosphate buffered saline (PBS) containing EDTA (2.5 mM final concentration). Plasma was stored at −80° C. for fluid assays.

Surface Marker Profiling

Blood was first centrifuged (10 minutes, 3000 G) to remove the plasma and resuspended to its original volume with phosphate buffered saline (PBS) containing EDTA (0.5%). For surface staining of eosinophils from whole blood, 50 l of blood were stained with the live/dead near infrared viability probe (Invitrogen, Carlsbad, Calif.) and several antibodies against surface determinants for 20 minutes at 4° C. in darkness. These antibodies included anti-CD3 (Invitrogen, Carlsbad, Calif.; clone: UCHT1), anti-CD14 (Invitrogen; clone: TüK4), and anti-CD16 (BD Biosciences, San Jose, Calif.; clone: 3G8). After staining, cells were washed with excess PBS containing EDTA (0.5%) and fetal calf serum (FCS, 5%), centrifuged (5 minutes, 490 G) and the supernatant was removed. Upon resuspension in 100 μl of PBS containing EDTA, cells were fixed with 2 ml of 1× Lyse/Fix Phosflow (BD Biosciences)

for 30 minutes at 4° C. in the dark and then centrifuged (5 minutes, 490 G).

Intracellular Phosphoepitope Profiling

For each sample, 50 μl of blood were stained with the live/dead near infrared viability probe and with antibodies that are resistant to methanol-based permeabilization (anti-CD3, and -CD16) for surface staining to identify granulocyte and CD3+ lymphocyte subsets. Cells were then washed with an excess of PBS containing EDTA (0.5%) and FCS (5%), centrifuged (5 minutes, 490 G), and resuspended. Subsequently, cells were fixed with 2 ml of 1× Lyse/Fix Phosflow Buffer (BD Biosciences), centrifuged (5 minutes, 490 G), and permeabilized with 200l of Perm Buffer III (BD Biosciences) for 30 minutes at 4° C. in darkness. Cells were then washed twice with an excess of PBS containing EDTA and centrifuged after each wash (5 minutes, 490 G). After permeabilization, cells were stained for the phosphoepitopes of interest for 20 minutes at 4° C. in darkness. The antibodies used included: anti-phospho-STAT1 (BD Biosciences; pY701; clone: 4a), -phospho-STAT4 (BD Biosciences; pY693; clone: 38/p-Stat4), -phospho-STAT6 (BD Biosciences; pY641; clone: 18). After staining, cells were washed with an excess of PBS containing EDTA and FCS and centrifuged (5 min, 490 G).

Data Acquisition by Flow Cytometry

Data for 100,000 cells per sample were acquired on a LSRII digital flow cytometer equipped with 4 lasers (535 nm, 488 nm, 633 nm, 405 nm), 2 light scatter detectors (yielding forward and side scatter data) and 18 fluorescent detectors (BD Biosciences). Compensation was done using single-stained beads or cells.

Cytokine and Chemokine Assays

Thirty-five cytokines and chemokines were assayed as part of a 35-plex: fibroblast growth factor basic FGF-β or FGF-2); eotaxin (1, 2, and 3); IL-1; IL-1β; IL-1 receptor antagonist (IL-1RA); IL-2; IL-4; IL-5; IL-6; IL-7; IL-8; IL-10; IL-12-p40; IL-12-p70; IL-13; IL-15; IL-17; IL-17F; epithelial cell-derived neutrophil-activating protein-78 (ENA78); granulocyte colony-stimulating factor (G-CSF); granulocyte-macrophage colony-stimulating factor (GM-CSF); growth-related oncogene-alpha GRO-α); interferon-gammaIFN-γ); interferon-inducible protein 10 (IP10); leptin; monocyte chemotactic protein-3 (MCP-3); monokine induced by gamma interferon (MIG); macrophage inflammatory protein 1 alpha (MIP-1α); macrophage inflammatory protein 1 beta (MIP-1β); neural growth factor (NGF); platelet-derived growth factor-BB (PDGF-BB); regulated upon activation, normal T cell expressed and secreted (RANTES); transforming growth factor beta (TGF-β); tumor necrosis factor alpha (TNF-α); tumor necrosis factor beta (TNF-β), and vascular endothelial growth factor (VEGF). Samples were tested and normalized with standard curves to ensure consistency and calibrations occurred before each run, as per manufacturer's instructions (Luminex Technologies, Austin, Tex.). Furthermore, each sample was run in duplicate for quality control. Plasma IgE levels were measured by Clinical Laboratories at Stanford Hospital and Clinics Statistical Analysis Statistical analysis was performed with the JMP8 software (SAS Institute, Cary, N.C.). The data distribution was assessed for normality using the Shapiro-Wilk test. Non parametric tests were used since the data were not normally distributed. Between-group comparisons were made using the Wilcoxon Rank Sum test. Correlation statistics were made using the non-parametric Spearman test. Differences were considered significant at a P value of less than or equal to 0.05. For Luminex data comparisons, the P value for significance was calculated using the Bonferroni correction, and differences were considered significant at a P value of less than or equal to 0.0014.

Discussion

We have shown that the baseline expression of intracellular phosphorylated forms of STAT1 and STAT6 within blood eosinophils, neutrophils, and CD3+ lymphocytes helps to distinguish between untreated EoE subjects and HC subjects. Furthermore, phospho-STAT1 and phospho-STAT6 levels in blood eosinophils also help to distinguish untreated EoE subjects from EoE subjects with therapy. Phospho-STAT6 levels in blood neutrophils correlate with a key disease parameter for EoE, the number of eosinophils per high-power field in esophageal tissues on biopsy. Furthermore, we show that plasma molecules do not appear to be predictive of therapeutic effect. Our findings demonstrate that blood cell-based assays are important for further mechanistic studies in EoE and in monitoring disease and management course.

These results also provide new insights into the pathophysiological mechanisms involved in EoE. Existing clinical tools for EoE often employ invasive EGD and biopsy procedures. Diagnosis of EoE is based upon pathologic findings of 15 or more eosinophils per high-power field in esophageal biopsy specimens. Here, we observe that levels of phospho-STAT6 in blood neutrophils of EoE subjects positively correlated with the number of eosinophils per high-power field in distal and proximal esophageal tissues. Importantly, these findings suggest that cellular-based measurements of phospho-STAT levels by means of whole blood staining and flow cytometry, a much less invasive and risky procedure than EGD and biopsy, could potentially serve as a novel clinical tool to aid in the diagnosis and prognosis of EoE.

Recent studies on EoE provide evidence that this disease is a mixed type immunological disorder involving both $T_H1$ and $T_H2$ responses. The family of STAT proteins mediates signaling by $T_H1$ and $T_H2$ cytokines and has been implicated in the development of inflammation and allergic diseases. STAT1 signaling involves the $T_H1$ cytokine IFN-γ, while STAT6 signaling involves the $T_H2$ cytokine IL-4. Previous work from our group on asthmatic subjects has demonstrated that allergic asthmatic subjects showed higher levels of phospho-STAT6 and lower levels of phospho-STAT1 in CD4+CD161+ T cells, whereas the reverse was true for non-allergic asthmatic subjects. However, our findings here demonstrate that for EoE subjects, phospho-STAT1 and phospho-STAT6 levels in blood eosinophils, neutrophils, and CD3+ lymphocytes were often positively correlated. These observations provide further support for the understanding of EoE as a mixed-type immunologic disorder.

Mechanistically, it is important then to explore the possible role of immune cells from blood, in particular eosinophils, neutrophils, and CD3+ lymphocytes, in EoE disease pathogenesis, and how signaling through STAT proteins may be involved. EoE is a disease characterized by high numbers of eosinophils in the esophagus, so it is perplexing as to why neutrophils and CD3+ lymphocytes in blood of subjects with this disease also show elevated levels of phospho-STATs. One possible explanation that warrants further investigation is that blood eosinophils, neutrophils, and also CD3+ lymphocytes may be involved in the signaling events that must occur to attract and maintain high numbers of eosinophils in the esophagus.

STAT1 signaling has been linked to IL-5 and STAT6 signaling has been shown to mediate the expression of eotaxin genes through known STAT6 binding sites in the eotaxin-1 and eotaxin-3 promoter sequences. The cytokine IL-5 and the eotaxin family of chemokines are known to be potent eosinophil chemoattractants that are important for eosinophil migration to the esophagus in EoE. Furthermore, STAT6 signaling involves IL-4 and can lead to IgE production, which is particularly relevant to EoE given the high rates of hypersensitivity to food and aeroallergens among patients with EoE. Taken together, these observations provide support for the possibility that STAT1 and STAT6 signaling may play a role in the mechanisms of EoE. Further studies will explore the modulation of STAT1 signaling in eosinophils by IL-5 as well as the modulation of eotaxin levels by STAT6 in EoE subjects. Moreover, most of the subjects with EoE in this study have food allergies and/or other allergic disorders. Further studies will investigate STAT6 signaling in EoE patients with atopic diseases such as food allergy or asthma, compared with non-atopic EoE patients.

As part of our search for less invasive ways to monitor EoE activity, we also performed fluid assays on plasma samples from EoE subjects and healthy subjects to look for relevant plasma disease indicators. In particular, we focused on plasma markers that are associated with STAT1 and STAT6 signaling. We found that levels of these plasma markers did not help to differentiate between EoE subjects with and without prescribed therapy.

These observations demonstrate the importance of cell-based measurements of phospho-STAT levels in immune cells from blood as potential new clinical tools for monitoring the disease and management course of EoE. In particular, phospho-STAT1 and phospho-STAT6 can be taken together as intracellular markers in eosinophils of EoE subjects to help monitor response to therapies. The success of the rapid and readily accessible flow cytometry method used here paves the way for the development of a much-needed less invasive blood assay to track treatment outcomes in patients with EoE.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

What is claimed is:

1. An ex vivo method for determining immunoglobulin-E (IgE)-mediated food allergy in a subject independent of exposing a whole blood sample from the subject to a stimulating allergen and regardless of whether the subject has a known allergy or predisposition to allergy, and for treating the subject if the subject is determined to have an allergic disease comprising:

(1) determining whether the subject has a food allergy by:
 (a) collecting from the subject a whole blood sample containing a live granulocyte population containing a live basophil population whose in vivo activation status has been preserved by not exposing the whole blood sample to a stimulating allergen;
 (b) labeling a portion of the whole blood sample of (a) with a labeling agent, wherein the labeling agent is an antibody coupled with a fluorophore, a chemical stain, a radioisotope, or a combination thereof, that is effective to label an intracellular signaling marker expressed by the live basophil population whose in vivo activation status has been preserved, thereby forming a labeled population of live basophils, wherein the intracellular signaling marker is phospho-SRc;
 (c) measuring an expression level of the phospho-SRc protein in the labeled live basophil population of granulocytes in (b) whose in vivo activation status has been preserved, wherein the measuring is carried out via flow cytometry or fluorescence-activated cell sorting (FACS);
 (d) collecting from a healthy control subject a whole blood sample containing a live granulocyte population containing a live basophil population whose in vivo activation status has been preserved;
 (e) labeling a portion of the whole blood sample of (d) with a labeling agent, wherein the labeling agent is an antibody coupled with a fluorophore, a chemical stain, a radioisotope, or a combination thereof, that is effective to label an intracellular signaling marker expressed by the live basophil population whose in vivo activation status has been preserved, thereby forming a labeled population of live basophils, wherein the intracellular signaling marker is phospho-SRc;
 (f) measuring an expression level of phospho-SRc in the labeled live basophil population of granulocytes in (e) whose in vivo activation status has been preserved, wherein the measuring is carried out via flow cytometry or fluorescence-activated cell sorting (FACS); and
 (g) determining if the subject has an immunoglobulin-E (IgE)-mediated food allergy by comparing the expression level of the intracellular signaling marker protein in the labeled live basophil population measured in (c) with the expression level of the intracellular signaling marker protein in the labeled live basophil population measured in (f), wherein the expression level of the intracellular signaling marker protein corresponds to an increase in number and/or activation state of the basophil population;
the expression level of one who has an allergic disease being characterized by an increased level of the intracellular signaling marker protein in the labeled live basophil population in the whole blood sample collected from the subject compared to the expression level of the intracellular signaling marker protein in the labeled live basophil population in the whole blood sample collected from the healthy control subject;
(2) once the subject is determined to have an immunoglobulin-E (IgE)-mediated food allergy in (g), identifying from a panel of food-based allergens one or more specific food-based allergens to which the subject produces an allergic response by repeating steps (a)-(g), wherein steps (a)-(g) further comprise (a') contacting the population of granulocytes in the whole blood sample with the one or more specific food-based allergens prior to labeling step (b); and (3) treating the subject with a therapeutically effective allergy treatment regimen, based on the specific food-based allergens identified in (2).

2. The method according to claim 1, further comprising monitoring effectiveness of the allergy treatment regimen in the subject, wherein the subject (i) has an allergic disease; and (ii) has been or is being treated with the allergy treatment regimen;

wherein, in collecting step (a), the whole blood sample collected before the allergy treatment regimen serves as a baseline control; and the expression level of one responsive to the allergy treatment regimen being characterized by a decreased level of the intracellular signaling marker protein in the live basophil population whose in vivo activation status has been preserved compared to the expression level of the intracellular signaling marker protein of the live basophil population in the baseline control.

3. The method according to claim 1, wherein collection step (a) is carried out via venipuncture.

4. The method according to claim 1, the basophil being characterized as expressing cell surface marker CD16 and negative for or expressing a low level of cell surface marker CD66b.

5. The method according to claim 1, wherein steps (b) through (g) are performed at 4° C.

* * * * *